(12) United States Patent
Nicholas et al.

(10) Patent No.: US 8,946,497 B1
(45) Date of Patent: Feb. 3, 2015

(54) UZM-39 ALUMINOSILICATE ZEOLITE

(71) Applicant: UOP LLC, Des Plaines, IL (US)

(72) Inventors: Christopher P. Nicholas, Evanston, IL (US); Mark A. Miller, Niles, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/507,941

(22) Filed: Oct. 7, 2014

Related U.S. Application Data

(60) Continuation of application No. 14/074,188, filed on Nov. 7, 2013, which is a division of application No. 13/714,528, filed on Dec. 14, 2012, now Pat. No. 8,642,823.

(60) Provisional application No. 61/578,909, filed on Dec. 22, 2011.

(51) Int. Cl.
| | | |
|---|---|---|
| *C07C 7/13* | (2006.01) | |
| *C07C 7/12* | (2006.01) | |
| *B01J 43/00* | (2006.01) | |
| *B01J 20/18* | (2006.01) | |
| *C07C 2/66* | (2006.01) | |
| *B01J 29/80* | (2006.01) | |
| *B01J 29/87* | (2006.01) | |

(52) U.S. Cl.
CPC . *B01J 20/18* (2013.01); *C07C 2/66* (2013.01); *B01J 29/80* (2013.01); *B01J 29/87* (2013.01); *C07C 2529/70* (2013.01)
USPC .......................... 585/820; 585/823; 585/824

(58) Field of Classification Search
USPC ......................................... 585/820, 823, 824
See application file for complete search history.

(56) References Cited

U.S. PATENT DOCUMENTS 5,013,337 A * 5/1991 Bedard et al. .................. 95/123

* cited by examiner

*Primary Examiner* — Thuan D Dang

(57) ABSTRACT

A new family of coherently grown composites of TUN and IMF zeotypes have been synthesized. These zeolites are represented by the empirical formula.

$$Na_nM_m^{k+}T_rAl_{1-x}E_xSi_yO_z$$

where "n" is the mole ratio of Na to (Al+E), M represents a metal or metals from zinc, Group 1, Group 2, Group 3 and or the lanthanide series of the periodic table, "m" is the mole ratio of M to (Al+E), "k" is the average charge of the metal or metals M, T is the organic structure directing agent or agents, and E is a framework element such as gallium. These zeolites are similar to TNU-9 and IM-5 but are characterized by unique compositions and synthesis procedures and have catalytic properties for carrying out various hydrocarbon conversion processes and separation properties for carrying out various separations.

2 Claims, 13 Drawing Sheets

UZM-39 ALUMINOSILICATE ZEOLITE

CROSS-REFERENCE TO RELATED APPLICATION

This application is a Continuation of copending application Ser. No. 14/074,188 filed Nov. 7, 2013, which application is a Division of U.S. Pat. No. 8,642,823 granted Feb. 4, 2014, which application claims priority from Provisional Application No. 61/578,909 filed Dec. 22, 2011, the contents of which are hereby incorporated by reference.

FIELD OF THE INVENTION

This invention relates to a new family of aluminosilicate zeolites designated UZM-39. They are represented by the empirical formula of:

$$Na_n M_m^{k+} T_r Al_{1-x} E_x Si_y O_z$$

where M represents a metal or metals from zinc or Group 1 (IUPAC 1), Group 2 (IUPAC 2), Group 3 (IUPAC 3) or the lanthanide series of the periodic table, T is the organic directing agent derived from reactants R and Q where R is an A,Ω-dihalosubstituted alkane such as 1,4-dibromobutane and Q is at least one neutral amine having 6 or fewer carbon atoms such as 1-methylpyrrolidine. E is a framework element such as gallium.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

One particular zeolite, designated TNU-9, was first disclosed by Hong et al. in 2004 (J. Am. Chem. Soc. 2004, 126, 5817-26) and then in a Korean Patent granted in 2005, KR 480229. This report and patent was followed by a full report of the synthesis in 2007 (J. Am. Chem. Soc. 2007, 129, 10870-85). These papers describe the synthesis of TNU-9 from the flexible dicationic structure directing agent, 1,4-bis(N-methylpyrrolidinium)butane dibromide in the presence of sodium. After the structure of TNU-9 was solved (Nature, 2006, 444, 79-81), the International Zeolite Association Structure Commission gave the code of TUN to this zeolite structure type, see Atlas of Zeolite Framework Types, which is maintained by the International Zeolite Association Structure Commission at http://www.iza-structure.org/databases/. The TUN structure type was found to contain 3 mutually orthogonal sets of channels in which each channel is defined by a 10-membered ring of tetrahedrally coordinated atoms. In addition, 2 different sizes of 10-membered ring channels exist in the structure.

Another particular zeolite, IM-5 was first disclosed by Benazzi, et al. in 1996 (FR96/12873; WO98/17581) who describe the synthesis of IM-5 from the flexible dicationic structure directing agent, 1,5-bis(N-methylpyrrolidinium) pentane dibromide or 1,6-bis(N-methylpyrrolidinium)hexane dibromide in the presence of sodium. After the structure of IM-5 was solved by Baerlocher et al. (Science, 2007, 315, 113-6), the International Zeolite Structure Commission gave the code of IMF to this zeolite structure type, see Atlas of Zeolite Framework Types. The IMF structure type was also found to contain three mutually orthogonal sets of channels in which each channel is defined by a 10-membered ring of tetrahedrally coordinated atoms, however, connectivity in the third dimension is interrupted every 2.5 nm, therefore diffusion is somewhat limited. In addition, multiple different sizes of 10-membered ring channels exist in the structure.

Applicants have successfully prepared a new family of materials designated UZM-39. The topology of the materials is similar to that observed for TNU-9 and IM-5. The materials are prepared via the use of a mixture of simple commercially available structure directing agents, such as 1,4-dibromobutane and 1-methylpyrrolidine, in concert with $Na^+$ using the Layered Material Conversion approach to zeolite synthesis (described below).

SUMMARY OF THE INVENTION

As stated, the present invention relates to a new aluminosilicate zeolite designated UZM-39. Accordingly, one embodiment of the invention is a coherently grown composite of TUN and IMF zeotypes having a three-dimensional framework of at least $AlO_2$ and $SiO_2$ tetrahedral units and an empirical composition in the as synthesized and anhydrous basis expressed by an empirical formula of:

$$Na_n M_m^{k+} T_r Al_{1-x} E_x Si_y O_z$$

where "n" is the mole ratio of Na to (Al+E) and has a value from approximately 0.05 to 0.5, M represents at least one metal selected from the group consisting of zinc, Group 1 (IUPAC 1), Group 2 (IUPAC 2), Group 3 (IUPAC 3), and the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having from 3 to 6 carbon atoms and Q is at least one neutral monoamine having 6 or fewer carbon atoms, "t" is the mole ratio of N from the organic structure directing agent or agents to (Al+E) and has a value of from about 0.5 to about 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

and is characterized in that it has TUN regions and IMF regions that are coherently aligned so that the $[010]_{TUN}$ zone axis and the $[001]_{IMF}$ zone axis are parallel to each other and there is continuity of crystal planes of type $(002)_{TUN}$ and $(060)_{IMF}$, where the indexing is referred to monoclinic $C_{2/m}$ and orthorhombic $C_{mem}$ unit cells for TUN and IMF respectively.

Another embodiment of the invention is a microporous crystalline zeolite having a three-dimensional framework of at least AlO$_2$ and SiO$_2$ tetrahedral units and an empirical composition in the as synthesized and anhydrous basis expressed by an empirical formula of:

$$Na_n M_m^{k+} T_t Al_{1-x} E_x Si_y O_z$$

where "n" is the mole ratio of Na to (Al+E) and has a value from approximately 0.05 to 0.5, M represents a metal or metals from Group 1 (IUPAC 1), Group 2 (IUPAC 2), Group 3 (IUPAC 3), the lanthanide series of the periodic table or zinc, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having between 3 and 6 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

and the zeolite is characterized in that it has the x-ray diffraction pattern having at least the d-spacings and intensities set forth in Table A1

TABLE A1

| 2θ | d (Å) | I/Io % |
|---|---|---|
| 7.17-7.21 | 12.25-12.31 | vw-m |
| 7.5-8.1* | 11.78-10.91 | w-m |
| 8.88 | 9.95 | m |
| 9.17 | 9.63 | w-m |
| 12.47-12.62 | 7.09-7.00 | w-m |
| 17.7 | 5.01 | vw-m |
| 22.8-23.2 | 3.90-3.83 | vs |
| 23.39-23.49 | 3.80-3.78 | m-s |
| 25.01-25.31 | 3.56-3.52 | m |
| 28.74-29.25 | 3.10-3.05 | w-m |
| 45.08-45.29 | 2.01-2.00 | w |

*composite peak consisting of multiple overlapping reflections

The zeolite is thermally stable up to a temperature of greater than 600° C. in one embodiment and at least 800° C. in another embodiment.

Another embodiment of the invention is a process using the Layered Material Conversion approach for preparing the crystalline microporous zeolite described above. The process comprises forming a reaction mixture containing reactive sources of Na, R, Q, Al, Si, seeds of a layered material L and optionally E and/or M and heating the reaction mixture at a temperature of about 150° C. to about 200° C., about 155° C. to about 190° C., or about 160° C. to about 180° C., for a time sufficient to form the zeolite. L does not have the same zeotype as the UZM-39 coherently grown composite. The reaction mixture has a composition expressed in terms of mole ratios of the oxides of:

$$a-bNa_2O:bM_{n/2}O:cRO:dQ:1-eAl_2O_3:eE_2O_3:fSiO_2:gH_2O$$

where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000. Additionally, the reaction mixture comprises from about 1 to about 10 wt.-% of seed zeolite L based on the amount of SiO$_2$ in the reaction mixture, e.g., if there is 100 g of SiO$_2$ in the reaction mixture, from about 1 to about 10 g of seed zeolite L would be added to the reaction mixture. With this number of reactive reagent sources, many orders of addition can be envisioned. Typically, the aluminum reagent is dissolved in the sodium hydroxide prior to adding the silica reagents. As can be seen in the examples, reagents R and Q can be added together or separately in many different orders of addition.

Yet another embodiment of the invention is a hydrocarbon conversion process using the above-described zeolite. The process comprises contacting the hydrocarbon with the zeolite at conversion conditions to give a converted hydrocarbon. Still another embodiment of the invention is a separation process using the above-described zeolite.

DETAILED DESCRIPTION OF THE INVENTION

Figure 1:
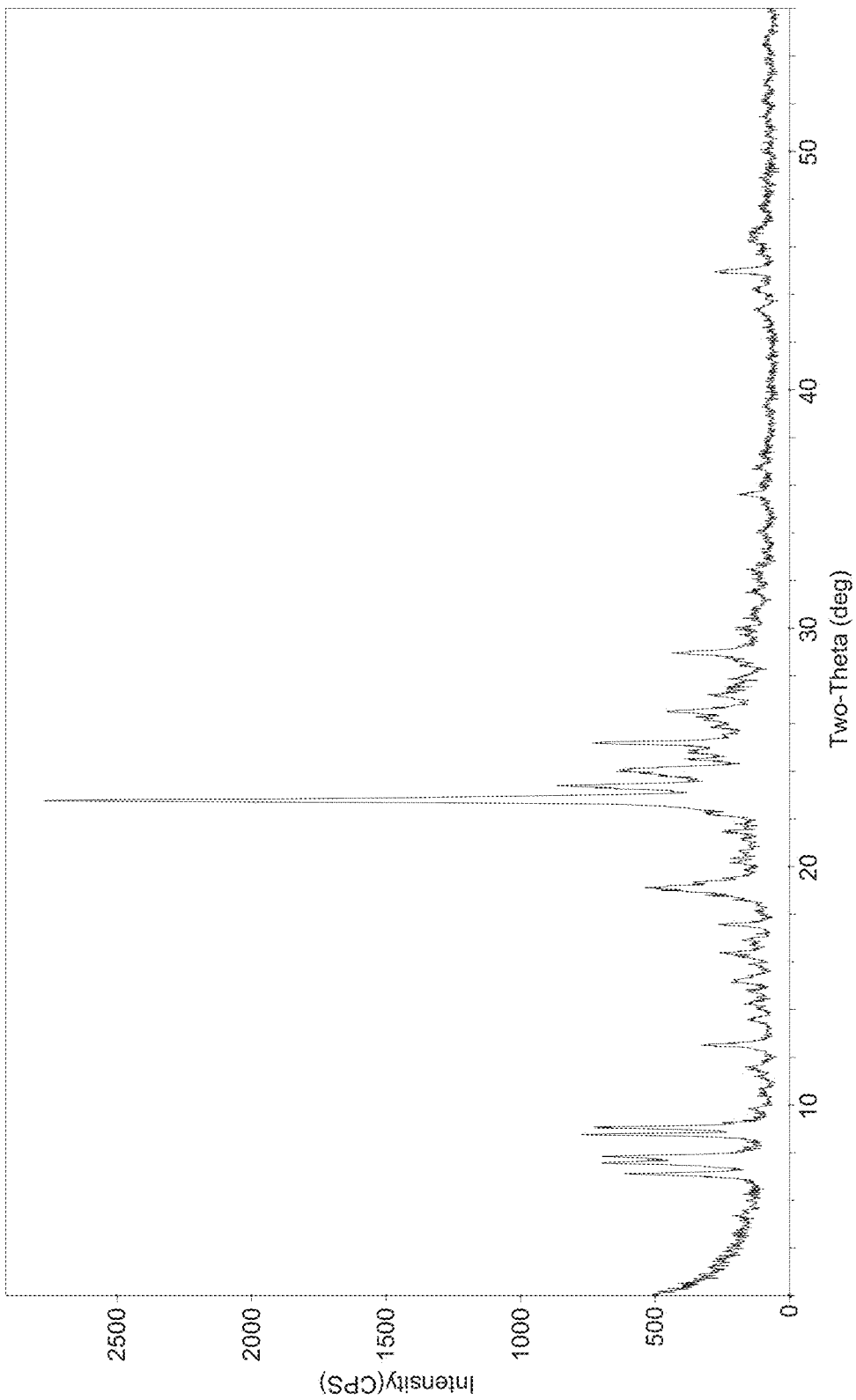
FIG. 1 is an XRD pattern of the UZM-39 zeolite formed in Example 1. This pattern shows the UZM-39 zeolite in the as-synthesized form.

Applicants have prepared an aluminosilicate zeolite whose topological structure is related to TUN as described in Atlas of Zeolite Framework Types, which is maintained by the International Zeolite Association Structure Commission at http://www.iza-structure.org/databases/, the member of which has been designated TNU-9. As will be shown in detail, UZM-39 is different from TNU-9 in a number of its characteristics including its x-ray diffraction pattern (XRD). UZM-39 is also related to IMF as described in the Atlas of Zeolite Framework Types, the member of which has been designated IM-5. As will be shown in detail, UZM-39 is different from TNU-9 and IM-5 in a number of its characteristics including its x-ray diffraction pattern. The instant microporous crystalline zeolite (UZM-39) has an empirical composition in the as synthesized and anhydrous basis expressed by an empirical formula of:

$$Na_n M_m^{k+} T_t Al_{1-x} E_x Si_y O_z$$

where "n" is the mole ratio of Na to (Al+E) and has a value from approximately 0.05 to 0.5, M represents a metal or metals selected from the group consisting of zinc, Group 1 (IUPAC 1), Group 2 (IUPAC 2), Group 3 (IUPAC 3), the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having between 3 and 6 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

where M is only one metal, then the weighted average valence is the valence of that one metal, i.e. +1 or +2. However, when more than one M metal is present, the total amount of:

$$M_m^{k+}=M_{m1}^{(k1)+}+M_{m2}^{(k2)+}+M_{m3}^{(k3)+}+M_{m4}^{(k4)+}+\ldots$$

and the weighted average valence "k" is given by the equation:

$$k = \frac{m1 \cdot k1 + m2 \cdot k2 + m3 \cdot k3 \ldots}{m1 + m2 + m3 \ldots}$$

In one embodiment, the microporous crystalline zeolite, UZM-39, is synthesized by a hydrothermal crystallization of a reaction mixture prepared by combining reactive sources of sodium, organic structure directing agent or agents T, aluminum, silicon, seeds of a layered material L, and optionally E, M, or both. The sources of aluminum include but are not limited to aluminum alkoxides, precipitated aluminas, aluminum metal, aluminum hydroxide, sodium aluminate, aluminum salts and alumina sols. Specific examples of aluminum alkoxides include, but are not limited to aluminum sec-butoxide and aluminum ortho isopropoxide. Sources of silica include but are not limited to tetraethylorthosilicate, colloidal silica, precipitated silica and alkali silicates. Sources of sodium include but are not limited to sodium hydroxide, sodium bromide, sodium aluminate, and sodium silicate.

T is the organic structure directing agent or agents derived from reactants R and Q where R is an A,Ω-dihalogen substituted alkane having between 3 and 6 carbon atoms and Q comprises at least one neutral monoamine having 6 or fewer carbon atoms. R may be an A,Ω-dihalogen substituted alkane having between 3 and 6 carbon atoms selected from the group consisting of 1,3-dichloropropane, 1,4-dichlorobutane, 1,5-dichloropentane, 1,6-dichlorohexane, 1,3-dibromopropane, 1,4-dibromobutane, 1,5-dibromopentane, 1,6-dibromohexane, 1,3-diiodopropane, 1,4-diiodobutane, 1,5-diiodopentane, 1,6-diiodohexane and combinations thereof. Q comprises at least one neutral monoamine having 6 or fewer carbon atoms such as 1-ethylpyrrolidine, 1-methylpyrrolidine, 1-ethylazetidine, 1-methylazetidine, triethylamine, diethylmethylamine, dimethylethylamine, trimethylamine, dimethylbutylamine, dimethylpropylamine, dimethylisopropylamine, methylethylpropylamine, methylethylisopropylamine, dipropylamine, diisopropylamine, cyclopentylamine, methylcyclopentylamine, hexamethyleneimine. Q may comprise combinations of multiple neutral monoamines having 6 or fewer carbon atoms.

L comprises at least one seed of a layered zeolite. Suitable seed zeolites are layered materials that are microporous zeolites with crystal thickness in at least one dimension of less than about 30 to about 50 nm. The microporous materials have pore diameters of less than about 2 nm. The seed layered zeolite is of a different zeotype than the UZM-39 coherently grown composite being synthesized. Examples of suitable layered materials include but are not limited to UZM-4M (U.S. Pat. No. 6,776,975), UZM-5 (U.S. Pat. No. 6,613,302), UZM-8 (U.S. Pat. No. 6,756,030), UZM-8HS (U.S. Pat. No. 7,713,513), UZM-26 (US-2010-0152023-A1), UZM-27 (U.S. Pat. No. 7,575,737), BPH, FAU/EMT materials, *BEA or zeolite Beta, members of the MWW family such as MCM-22P and MCM-22, MCM-36, MCM-49, MCM-56, ITQ-1, ITQ-2, ITQ-30, ERB-1, EMM-10P and EMM-10, SSZ-25, and SSZ-70 as well as smaller microporous materials such as PREFER (pre ferrierite), NU-6 and the like.

M represents at least one exchangeable cation of a metal or metals from Group 1 (IUPAC 1), Group 2 (IUPAC 2), Group 3 (IUPAC 3) or the lanthanide series of the periodic table and or zinc. Specific examples of M include but are not limited to lithium, potassium, rubidium, cesium, magnesium, calcium, strontium, barium, zinc, yttrium, lanthanum, gadolinium, and mixtures thereof. Reactive sources of M include, but are not limited to, the group consisting of halide, nitrate, sulfate, hydroxide, or acetate salts. E is an element selected from the group consisting of gallium, iron, boron and combinations thereof, and suitable reactive sources include, but are not limited to, boric acid, gallium oxyhydroxide, gallium nitrate, gallium sulfate, ferric nitrate, ferric sulfate, ferric chloride and mixtures thereof.

The reaction mixture containing reactive sources of the desired components can be described in terms of molar ratios of the oxides by the formula:

$$a\text{-}b\mathrm{Na_2O}{:}b\mathrm{M}_{n/2}\mathrm{O}{:}c\mathrm{RO}{:}d\mathrm{Q}{:}1\text{-}e\mathrm{Al_2O_3}{:}e\mathrm{E_2O_3}{:}f\mathrm{SiO_2}{:}g\mathrm{H_2O}$$

where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000. Additionally in the reaction mixture is from about 1 to about 10 wt.-% of seed zeolite L based on the amount of SiO$_2$ in the reaction, e.g., if there is 100 g of SiO$_2$ in the reaction mixture, from about 1 to about 10 g of seed zeolite L would be added. The examples demonstrate a number of specific orders of addition for the reaction mixture which lead to UZM-39. However, as there are at least 6 starting materials, many orders of addition are possible. For example, the seed crystals L can be added as the last ingredient to the reaction mixture, to the reactive Si source, or at other suitable points. Also, if alkoxides are used, it is preferred to include a distillation or evaporative step to remove the alcohol hydrolysis products. While the organic structure directing agents R and Q can be added separately or together to the reaction mixture at a number of points in the process, it is preferred to mix R and Q together at room temperature and add the combined mixture to a cooled mixture of reactive Si, Al and Na sources maintained at 0-10° C. Alternatively, the mixture of R and Q, after mixing at room temperature, could be cooled and the reactive sources of Si, Al, and Na added to the organic structure directing agent mixture while maintaining a temperature of 0-10° C. In an alternative embodiment, the reagents R and Q could be added, separately or together, to the reaction mixture at room temperature.

The reaction mixture is then reacted at a temperature of about 150° C. to about 200° C., about 155° C. to about 190° C., or about 160° C. to about 180° C., for a period of about 1 day to about 3 weeks and preferably for a time of about 3 days to about 12 days in a stirred, sealed reaction vessel under autogenous pressure. After crystallization is complete, the solid product is isolated from the heterogeneous mixture by means such as filtration or centrifugation, and then washed with deionized water and dried in air at ambient temperature up to about 100° C.

The as-synthesized coherently grown composite of TUN and IMF zeotypes, UZM-39, is characterized by the x-ray diffraction pattern, having at least the d-spacings and relative intensities set forth in Tables A1-A3 below. Diffraction patterns herein were obtained using a typical laboratory powder diffractometer, utilizing the K$_\alpha$ line of copper; Cu K alpha. From the position of the diffraction peaks represented by the angle 2theta, the characteristic interplanar distances d$_{hkl}$ of the sample can be calculated using the Bragg equation. The intensity is calculated on the basis of a relative intensity scale attributing a value of 100 to the line representing the strongest peak on the X-ray diffraction pattern, and then: very weak (vw) means less than 5; weak (w) means less than 15; medium (m) means in the range 15 to 50; strong (s) means in the range 50 to 80; very strong (vs) means more than 80. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular coherently grown composite structures or for samples with crystals which are small enough to cause significant broadening of the X-rays. This can also be the case when the equipment or operating conditions used to produce the diffraction pattern differ significantly from those used in the present case.

Figure 3:
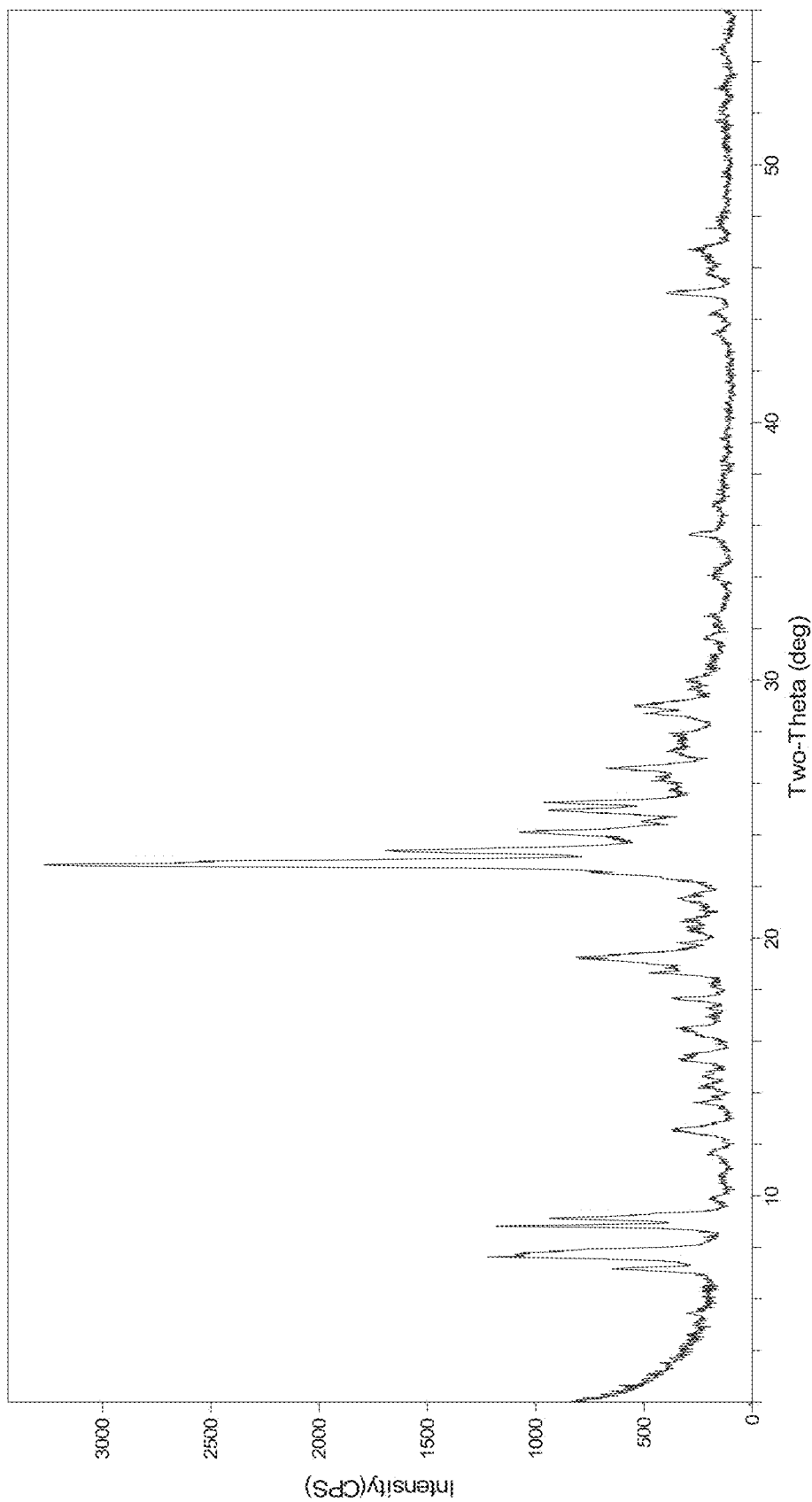
FIG. 3 is an XRD pattern of the UZM-39 zeolite formed in Example 16. This pattern shows the UZM-39 zeolite in the as-synthesized form.
Figure 5:
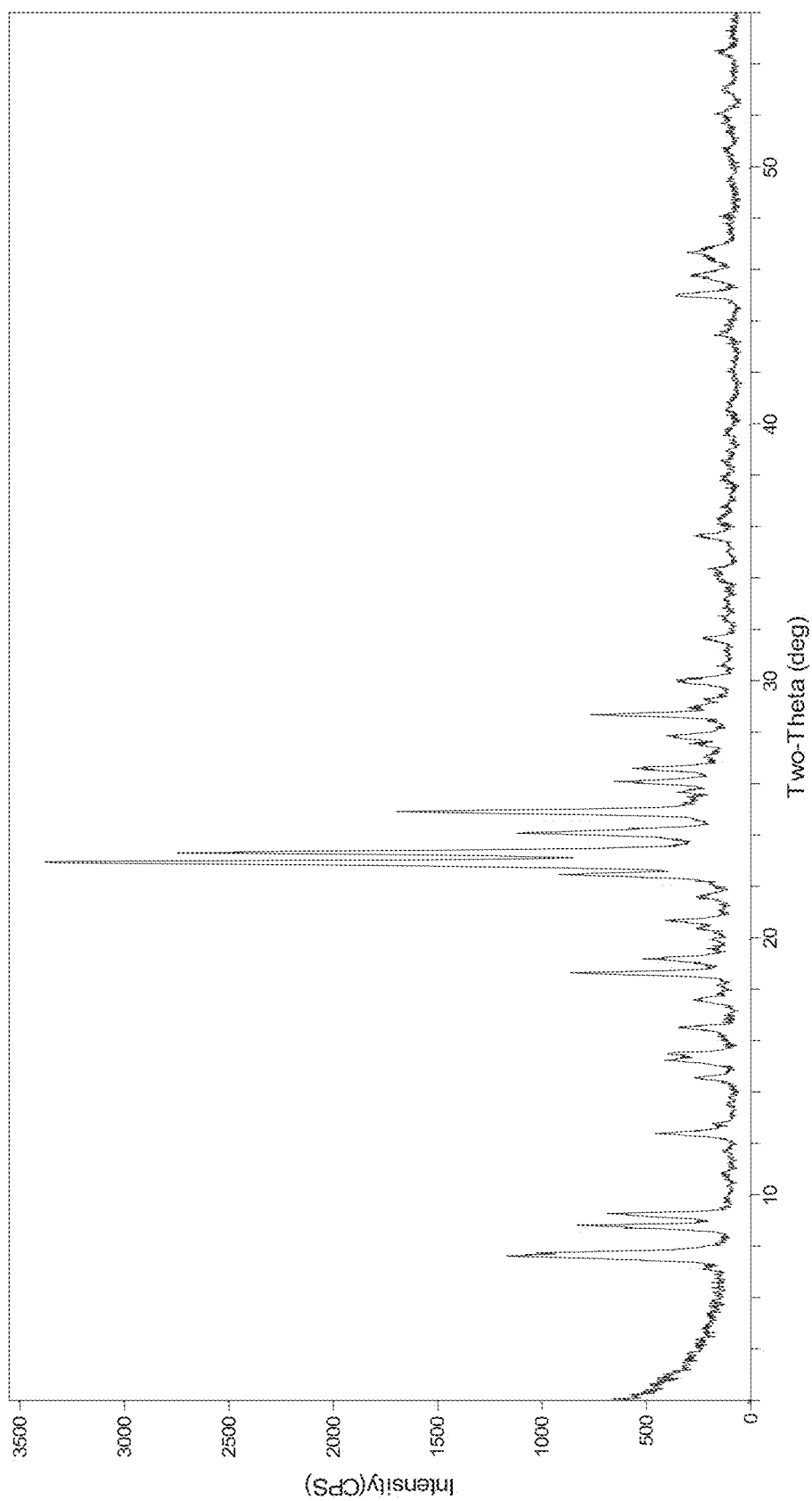
FIG. 5 is an XRD pattern of the UZM-39 zeolite formed in Example 28. This pattern shows the UZM-39 zeolite in the as-synthesized form.

The X-ray diffraction pattern for UZM-39 contains many peaks. Examples of the x-ray diffraction patterns for various as-synthesized UZM-39 products are shown in FIGS. 1, 3, and 5. Those peaks characteristic of UZM-39 are shown in Tables A1-A3 for various coherently grown composite structures. Additional peaks, particularly those of very weak intensity, may also be present. All peaks of medium or higher intensity present in the UZM-39 family of coherently grown composite structures are represented in at least Table A3.

Table A1 contains selected d-spacings and relative intensities of the UZM-39 X-ray diffraction pattern. The relative intensities are shown as a range covering UZM-39 materials with varying relative amounts of TUN and IMF zeotypes.

TABLE A1

| 2θ | d (Å) | I/Io % |
|---|---|---|
| 7.17-7.21 | 12.25-12.31 | vw-m |
| 7.5-8.1* | 11.78-10.91 | w-m |
| 8.88 | 9.95 | m |
| 9.17 | 9.63 | w-m |
| 12.47-12.62 | 7.09-7.00 | w-m |
| 17.7 | 5.01 | vw-m |
| 22.8-23.2 | 3.90-3.83 | vs |
| 23.39-23.49 | 3.80-3.78 | m-s |
| 25.01-25.31 | 3.56-3.52 | m |
| 28.74-29.25 | 3.10-3.05 | w-m |
| 45.08-45.29 | 2.01-2.00 | w |

*composite peak consisting of multiple overlapping reflections

The zeolite may be further characterized by the x-ray diffraction pattern having at least the d-spacings and intensities set forth in Table A2 where the d-spacings and intensities are provided at different relative concentrations of the components of the coherently grown composite structure.

TABLE A2

| I high TUN, low IMF | | | II med TUN, med IMF | | | III low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 7.21 | 12.25 | w-m | 7.17 | 12.31 | w-m | 7.21 | 12.25 | vw |
| 7.5-8.1* | 11.78-10.91 | w-m | 7.5-8.1* | 11.78-10.91 | w-m | 7.5-8.1* | 11.78-10.91 | w-m |
| 8.88 | 9.95 | m | 8.88 | 9.95 | s | 8.88 | 9.95 | m |
| 9.17 | 9.63 | m | 9.16 | 9.65 | m | 9.17** | 9.63 | w-m |
| 9.34** | 9.46 | vw-w | 9.30 | 9.50 | m | 9.33 | 9.47 | m |
| 12.62 | 7.00 | w | 12.50 | 7.08 | w-m | 12.47 | 7.09 | w-m |
| 17.70 | 5.01 | vw-w | 17.72 | 5.00 | w-m | 17.70 | 5.01 | vw-w |
| 19.20 | 4.62 | w-m | 22.8-23.2* | 3.90-3.83 | vs | 18.71 | 4.74 | w-m |

TABLE A2-continued

| I<br>high TUN, low IMF | | | II<br>med TUN, med IMF | | | III<br>low TUN, high IMF | | |
|---|---|---|---|---|---|---|---|---|
| 2-Theta | d(†) | I/Io % | 2-Theta | d(†) | I/Io % | 2-Theta | d(†) | I/Io % |
| 22.89 | 3.88 | vs | 23.43 | 3.79 | s | 22.55 | 3.94 | m |
| 23.49 | 3.78 | m | 25.12 | 3.54 | m | 23.03 | 3.86 | vs |
| 25.31 | 3.52 | m | 28.74-29.25* | 3.10-3.05 | w-m | 23.39 | 3.80 | s |
| 29.10 | 3.07 | w | 45.29 | 2.00 | w | 25.01 | 3.56 | m |
| 45.08 | 2.01 | w | | | | 28.76 | 3.10 | w-m |
| | | | | | | 45.08 | 2.01 | w |

*composite peak consisting of multiple overlapping reflections
**typically a shoulder The zeolite may be yet further characterized by the x-ray diffraction pattern having at least the d-spacings and intensities set forth in Table A3 where the d-spacings and intensities are provided at different relative concentrations of the components of the coherently grown composite structure.

TABLE A3

| I<br>high TUN, low IMF | | | II<br>med TUN, med IMF | | | III<br>low TUN, high IMF | | |
|---|---|---|---|---|---|---|---|---|
| 2-Theta | d(†) | I/Io % | 2-Theta | d(†) | I/Io % | 2-Theta | d(†) | I/Io % |
| 7.21 | 12.25 | w-m | 7.17 | 12.31 | w-m | 7.21 | 12.22 | vw |
| 7.5-8.1* | 11.78-10.91 | w-m | 7.5-8.1* | 11.78-10.91 | w-m | 7.5-8.1* | 11.78-10.91 | w-m |
| 8.88 | 9.95 | m | 8.88 | 9.95 | m-s | 8.88 | 9.95 | m |
| 9.17 | 9.63 | m | 9.16 | 9.65 | m | 9.17** | 9.63 | w-m |
| 9.34** | 9.46 | vw-w | 9.30 | 9.50 | m | 9.33 | 9.47 | m |
| 9.98 | 8.85 | vw | 12.50 | 7.08 | w-m | 12.47 | 7.09 | w-m |
| 11.68 | 7.57 | vw | 15.27 | 5.80 | vw-w | 12.85 | 6.88 | vw |
| 12.62 | 7.00 | w | 15.58 | 5.68 | w | 14.62 | 6.05 | vw-w |
| 13.69 | 6.46 | vw-w | 17.70 | 5.01 | vw-w | 15.27 | 5.80 | w |
| 15.33 | 5.77 | vw-w | 18.72 | 4.74 | vw-m | 15.57 | 5.68 | w |
| 16.48 | 5.37 | vw-w | 19.28 | 4.60 | w | 16.60 | 5.34 | w |
| 17.01 | 5.20 | vw | 22.61** | 3.93 | w-m | 17.70 | 5.01 | vw-w |
| 17.70 | 5.01 | vw-w | 22.8-23.2* | 3.90-3.83 | vs | 18.71 | 4.74 | w-m |
| 19.20 | 4.62 | w-m | 23.43 | 3.79 | s | 19.30 | 4.59 | w |
| 21.59 | 4.11 | vw-w | 24.20 | 3.68 | m | 22.55 | 3.94 | m |
| 22.61** | 3.93 | w-m | 25.12 | 3.54 | m | 22.86** | 3.89 | m-s |
| 22.89 | 3.88 | vs | 26.34 | 3.38 | w-m | 23.03 | 3.86 | vs |
| 23.49 | 3.78 | m | 26.75 | 3.33 | w-m | 23.39 | 3.80 | s |
| 23.93 | 3.72 | vw-w | 28.74-29.25* | 3.10-3.05 | w-m | 24.17 | 3.68 | m |
| 24.13 | 3.68 | m | 35.72 | 2.51 | vw-w | 25.01 | 3.56 | m |
| 24.64 | 3.61 | w | 45.29 | 2.00 | w | 26.19 | 3.40 | vw-w |
| 24.93 | 3.57 | w | 45.62-47.19* | 1.99-1.92 | vw-w | 26.68 | 3.34 | w-m |
| 25.31 | 3.52 | m | | | | 28.76 | 3.10 | w-m |
| 26.62 | 3.35 | w | | | | 35.72 | 2.51 | vw-w |
| 29.10 | 3.07 | w | | | | 45.08 | 2.01 | w |
| 35.72 | 2.51 | vw-w | | | | 45.62-47.19* | 1.99-1.92 | vw-w |
| 45.08 | 2.01 | w | | | | | | |
| 45.62-47.19* | 1.99-1.92 | vw-w | | | | | | |

*composite peak consisting of multiple overlapping reflections
**Typically a shoulder In Tables A2 and A3, the term "high" refers to about 60 to about 95 mass-% of the specified component, the term "med" refers to about 25 to about 70 mass-% of the specified component, and the term "low" refers to about 5 to about 40 mass-% of the specified component. Some peaks may be shoulders on more intense peaks, and some peaks may be a composite peak consisting of multiple overlapping reflections.

As will be shown in detail in the examples, the UZM-39 material is thermally stable up to a temperature of at least 600° C. and in another embodiment, up to at least 800° C. Also as shown in the examples, the UZM-39 material may have a micropore volume as a percentage of total pore volume of greater than 60%.

Characterization of the UZM-39 product by high-resolution scanning electron microscopy shows that the UZM-39 forms in lathes which assemble into rectangular rod particles, often with a starburst cluster arrangement. The starburst cluster rods of UZM-39 can be seen in the scanning electron microscopy results for two particular UZM-39 products in FIG. 7 and in FIG. 8.

Figure 9:
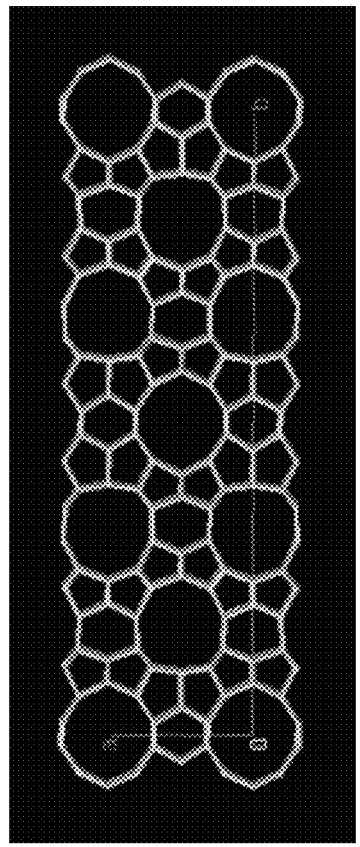
FIG. 9 shows a wireframe representation of the TUN framework in the AC plane (left). Each vertex is a T-site and in the middle of each stick is an oxygen atom. A wireframe representation of the IMF framework in the AB plane is shown to the right. Along these projections, both the TUN and IMF frameworks contain nearly identical projections of chains of 5-rings connected by 6-rings and 10-ring channels.
Figure 9:
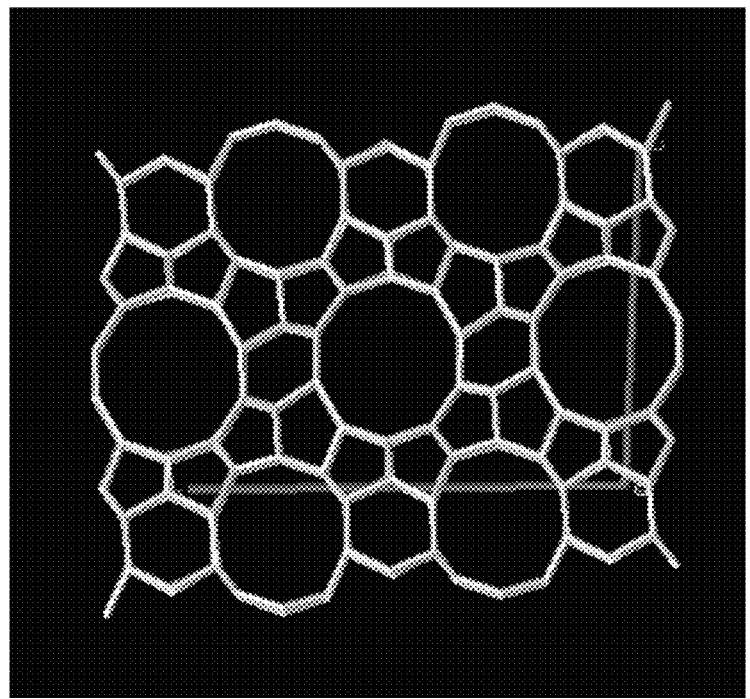

UZM-39 is a coherently grown composite structure of TUN and IMF zeotypes. By coherently grown composite structure is meant that both structures are present in a major portion of the crystals in a given sample. This coherently grown composite structure is possible when the two zeotypic structures have nearly identical spacial arrangements of atoms along at least a planar projection of their crystal structure and possess similar pore topologies. FIG. 9 shows a wireframe representation of the TUN framework in the AC plane (left). Each vertex is a tetrahedral site (or T-site) and in the middle of each stick is a corner-shared oxygen atom. A wireframe representation of the IMF framework in the AB plane is shown on the right of FIG. 9. Along these projections, both the TUN and IMF zeotypes contain nearly identical projections of chains of 5-rings connected by 6-rings and 10-rings which form channels running perpendicular to the plane.

As both the TUN and IMF zeotypes are 3-dimensional 10-ring zeolites and have nearly identical projections in one plane, the two structures can thereby coherently grow off crystals of the other structure with interfaces at the compatible planes to form a coherently grown composite structure.

A coherently grown composite structure is not a physical mixture of the two molecular sieves. Electron diffraction, transmission electron microscopy and x-ray diffraction analysis are employed to show that a material is a coherently grown composite structure instead of a physical mixture. Usually the combination of electron diffraction and TEM imaging is most definitive in determining whether one has produced a coherently grown composite structure because it provides direct evidence of the existence of both structures within one crystal.

Since the coherently grown composite structure zeolites of this invention can have varying amounts of the two structure types, it is to be understood that the relative intensity and line width of some of the diffraction lines will vary depending on the amount of each structure present in the coherently grown composite structure. Although the degree of variation in the x-ray powder diffraction patterns is theoretically predictable for specific structures, the more likely mode of a coherently grown composite structure is random in nature and therefore difficult to predict without the use of large hypothetical models as bases for calculation.

Unlike a physical mixture of TNU-9 and IM-5, transmission electron microscopy (TEM) analysis using high resolution imaging and computed optical diffractograms shows that UZM-39 is comprised of a coherently grown composite structure of TUN and IMF zeotypes.

Figure 10:
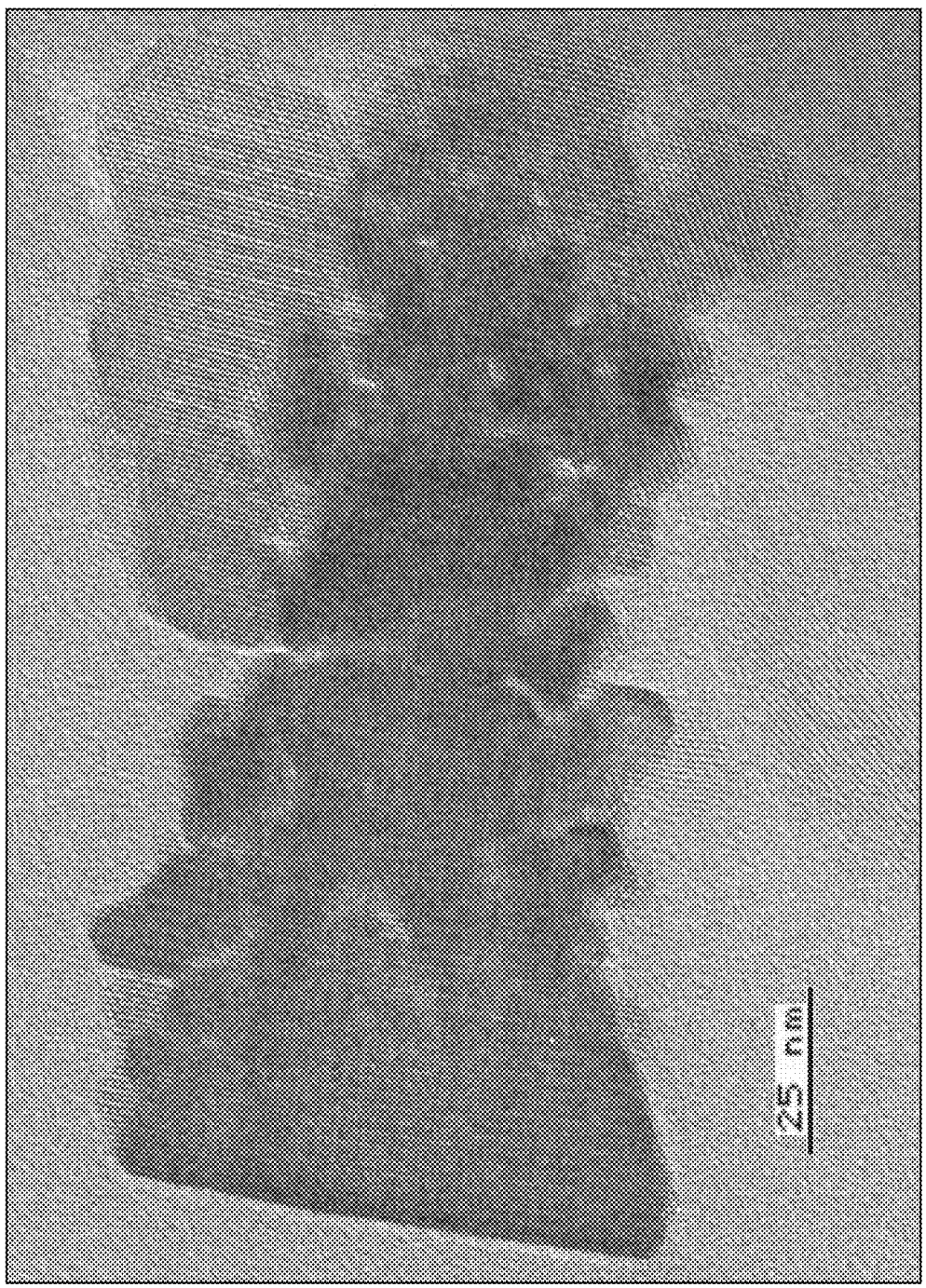
FIG. 10 shows the results of transmission electron microscopy characterization of the UZM-39 product of Example 17 using high resolution imaging and computed optical diffractograms. The results show that UZM-39 is comprised of a coherently grown composite structure of TUN and IMF zeotypes.

In FIG. 10, TEM analysis of a cross sectioned rod particle from the product of Example 17 shows that areas with TUN and IMF structure occur as coherent sub-regions within an effectively single-crystalline zeolite particle. On the left side of FIG. 11, electron diffraction analysis of the left side of the particle shown in FIG. 10 shows an electron diffraction pattern which can be indexed to the 002 plane of TUN. On the right side of FIG. 11, the electron diffraction pattern from the right side of the particle shown in FIG. 10 is shown. This pattern can be indexed to the 060 plane of IMF. The TUN regions and IMF regions are coherently aligned such that the [010]$_{TUN}$ zone axis and the [001]$_{IMF}$ zone axis are parallel to each other and there is continuity of crystal planes of type (002)$_{TUN}$ and (060)$_{IMF}$, where the indexing is referred to monoclinic C$_{2/m}$ and orthorhombic C$_{mem}$ unit cells for TUN and IMF respectively (details of structures found on IZA website). In spite of the presence of the two zeotypes in different portions of the particle, the image does not show any distinct boundary delineating separate crystals of TUN and IMF, indicating that the particle is a coherently grown composite.

Additionally, UZM-39 zeolite can be characterized by Rietveld analysis of the XRD pattern. Rietveld analysis is a least-squares approach developed by Rietveld (*Journal of Applied Crystallography* 1969, 2: 65-71) to refine a theoretical line XRD profile until it matches the measured XRD pattern as closely as possible and is the preferred method of deriving structural information from samples such as UZM-39 which contain strongly overlapping reflections. It is often used to quantify the amounts of two different phases in a XRD diffractogram. The accuracy of the Rietveld method is determined by parameters such as crystallite size (peak broadening), peak shape function, lattice unit cell constants and background fits. For the samples shown in the examples, applicants have determined the error in the reported value to be ±5% under the conditions used. Applicants have also determined that the Rietveld model used was unable to quantify the amounts of minority composite structure phase component at values less than 10%, but visually, amounts of the minority component can be seen at levels greater than 5% by comparing against the model patterns. Table 1 shows Rietveld refinement results on various UZM-39 samples from the examples and shows that UZM-39 contains greater than 0 and less than 100 wt. % IMF zeotype and less than 100 wt. % and greater than 0 wt. % TUN zeotype. In another embodiment, UZM-39 contains greater than 5 and less than 95 wt. % IMF zeotype and less than 95 wt. % and greater than 5 wt. % TUN zeotype, and in yet another embodiment, UZM-39 contains greater than 10 and less than 90 wt. % IMF zeotype and less than 90 wt. % and greater than 10 wt. % TUN zeotype. As can be seen in Table 1 and examples, a wide range of coherently grown composite structures are possible by modifying the synthesis conditions.

As synthesized, the UZM-39 material will contain some exchangeable or charge balancing cations in its pores. These exchangeable cations can be exchanged for other cations, or in the case of organic cations, they can be removed by heating under controlled conditions. It is also possible to remove some organic cations from the UZM-39 zeolite directly by ion exchange. The UZM-39 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination, ion-exchange and calcination and on an anhydrous basis, the microporous crystalline zeolite UZM-39 has a three-dimensional framework of at least AlO$_2$ and SiO$_2$ tetrahedral units and an empirical composition in the hydrogen form expressed by an empirical formula of

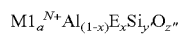

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

In the hydrogen form, after calcination, ion-exchange and calcination to remove NH$_3$, UZM-39 displays the XRD pattern shown in Table B1-B3. Those peaks characteristic of UZM-39 are shown in Tables B1-B3 for various coherently grown composite structures. Additional peaks, particularly those of very weak intensity, may also be present. All peaks of medium or higher intensity present in the UZM-39 family of coherently grown composite structures are represented in at least Tables B3.

Table B1 contains selected d-spacings and relative intensities of the hydrogen form of UZM-39 X-ray diffraction pattern. The relative intensities are shown as a range covering UZM-39 materials with varying relative amounts of TUN and IMF zeotypes.

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |

TABLE B1-continued

| 2θ | d (Å) | I/Io % |
|---|---|---|
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections

The zeolite may be further characterized by the x-ray diffraction pattern having at least the d-spacings and intensities set forth in Table B2 where the d-spacings and intensities are provided at different relative concentrations of the components of the coherently grown composite structure.

TABLE B2

| A high TUN, low IMF | | | B med TUN, med IMF | | | C low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 7.12 | 12.40 | w-m | 7.11 | 12.42 | w-m | 7.16 | 12.25 | vw-w |
| 7.5-8.1* | 11.78-10.91 | m | 7.5-8.1* | 11.78-10.91 | m-s | 7.5-8.1* | 11.78-10.91 | m-s |
| 8.84 | 10.00 | m-s | 8.84 | 10.00 | m-s | 8.84 | 10.00 | m-s |
| 9.06 | 9.75 | m | 9.08 | 9.73 | m | 9.06** | 9.75 | w |
| 9.24** | 9.56 | vw-w | 9.24 | 9.56 | m | 9.24 | 9.56 | m |
| 12.53 | 7.06 | w | 12.48 | 7.09 | m | 12.46 | 7.10 | m |
| 22.89 | 3.88 | vs | 22.56** | 3.94 | w-m | 22.56 | 3.94 | w-m |
| 23.40 | 3.80 | m | 22.75-23.2* | 3.90-3.83 | vs | 23.06 | 3.85 | vs |
| 24.23 | 3.67 | w-m | 23.40 | 3.80 | s | 23.40 | 3.80 | s |
| 25.22 | 3.53 | m | 24.17 | 3.68 | m | 24.12 | 3.69 | m |
| 29.08 | 3.07 | w-m | 24.92-25.37* | 3.57-3.51 | m | 25.06 | 3.55 | m |
| 45.36 | 2.00 | w | 28.71-29.27* | 3.11-3.05 | w-m | 28.82 | 3.10 | w-m |
| | | | 45.34 | 2.00 | w | 45.32 | 2.00 | w |

*composite peak consisting of multiple overlapping reflections
**Typically a shoulder The zeolite may be yet further characterized by the x-ray diffraction pattern having at least the d-spacings and intensities set forth in Table B3 where the d-spacings and intensities are provided at different relative concentrations of the components of the coherently grown composite structure.

TABLE B3

| I high TUN, low IMF | | | II med TUN, med IMF | | | III low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 7.12 | 12.40 | w-m | 7.11 | 12.42 | w-m | 7.16 | 12.25 | vw-w |
| 7.5-8.1* | 11.78-10.91 | m | 7.5-8.1* | 11.78-10.91 | m-s | 7.5-8.1* | 11.78-10.91 | m-s |
| 8.84 | 10.00 | m-s | 8.84 | 10.00 | m-s | 8.84 | 10.00 | m-s |
| 9.06 | 9.75 | m | 9.08 | 9.73 | m | 9.06** | 9.75 | w |
| 9.24** | 9.56 | vw-w | 9.24 | 9.56 | m | 9.24 | 9.56 | m |
| 12.53 | 7.06 | w | 11.76 | 7.52 | vw-w | 11.76 | 7.52 | vw-w |
| 14.38 | 6.15 | w | 12.48 | 7.09 | m | 12.46 | 7.10 | m |
| 14.64 | 6.05 | vw | 14.38 | 6.15 | vw-w | 14.38 | 6.15 | vw |
| 15.26 | 5.80 | vw-w | 14.64 | 6.05 | vw-w | 14.64 | 6.05 | w |
| 15.52 | 5.70 | vw | 15.26 | 5.80 | w | 15.26 | 5.80 | w |
| 16.46 | 5.38 | vw | 15.52 | 5.70 | w-m | 15.52 | 5.70 | w-m |
| 17.72 | 5.00 | w | 16.50 | 5.37 | vw-w | 16.58 | 5.34 | w |
| 22.56** | 3.94 | vw-w | 17.72 | 5.00 | w-m | 17.72 | 5.00 | w-m |
| 22.89 | 3.88 | vs | 18.64 | 4.76 | vw-w | 18.64 | 4.76 | w |
| 23.06** | 3.85 | w-m | 22.56** | 3.94 | w-m | 22.56 | 3.94 | w-m |
| 23.40 | 3.80 | m | 22.75-23.2* | 3.90-3.83 | vs | 23.06 | 3.85 | vs |
| 23.82 | 3.73 | w-m | 23.40 | 3.80 | s | 23.40 | 3.80 | s |
| 24.23 | 3.67 | w-m | 24.17 | 3.68 | m | 24.12 | 3.69 | m |
| 24.70 | 3.60 | w-m | 24.70 | 3.60 | w-m | 25.06 | 3.55 | m |
| 25.22 | 3.53 | m | 24.92-25.37* | 3.57-3.51 | m | 26.16 | 3.40 | vw-w |

TABLE B3-continued

| I high TUN, low IMF | | | II med TUN, med IMF | | | III low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 26.51 | 3.36 | w-m | 26.32 | 3.38 | w | 26.74 | 3.33 | w-m |
| 29.08 | 3.07 | w-m | 26.76 | 3.33 | w-m | 28.82 | 3.10 | w-m |
| 35.86 | 2.50 | vw-w | 28.71-29.27* | 3.11-3.05 | w-m | 30.12 | 2.96 | w |
| 45.36 | 2.00 | w | 30.13 | 2.96 | vw-w | 35.86 | 2.50 | vw-w |
| 45.66-47.37* | 1.98-1.91 | vw-w | 35.86 | 2.50 | vw-w | 45.32 | 2.00 | w |
|  |  |  | 45.34 | 2.00 | w | 45.66-47.37* | 1.98-1.91 | vw-w |
|  |  |  | 45.66-47.37* | 1.98-1.91 | vw-w |  |  |  |

*composite peak consisting of multiple overlapping reflections
**Typically a shoulder In Tables B2 and B3, the term "high" refers to about 60 to about 95 mass-% of the specified component, the term "med" refers to about 25 to about 70 mass-% of the specified component, and the term "low" refers to about 5 to about 40 mass-% of the specified component. Some peaks may be shoulders on more intense peaks, and some peaks may be a composite peak consisting of multiple overlapping reflections.

After acid treating, such as exposure to $HNO_3$ or $H_2SiF_6$, and on an anhydrous basis, the microporous crystalline zeolite UZM-39 has a three-dimensional framework of at least $AlO_2$ and $SiO_2$ tetrahedral units and an empirical composition in the acid treated form expressed by an empirical formula of

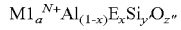

$$M1_a^{N+}Al_{(1-x)}E_xSi_{y'}O_{z''}$$

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

Similar to the as-synthesized material, the modified UZM-39 materials are thermally stable up to a temperature of at least 600° C. and in another embodiment, up to at least 800° C. and may have a micropore volume as a percentage of total pore volume of greater than 60%.

By virtually pure silica is meant that virtually all the aluminum and/or the E metals have been removed from the framework. It is well known that it is virtually impossible to remove all the aluminum and/or E metal. Numerically, a zeolite is virtually pure silica when y' has a value of at least 3,000, preferably 10,000 and most preferably 20,000. Thus, ranges for y' are from 9 to 3,000; from greater than 20 to about 3,000; from 9 to 10,000; from greater than 20 to about 10,000; from 9 to 20,000; and from greater than 20 to about 20,000.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline UZM-39 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species. The separation process may comprise contacting at least two components with the UZM-39 zeolite material to generate at least one separated component.

The UZM-39 zeolite of this invention can also be used as a catalyst or catalyst support in various hydrocarbon conversion processes. Hydrocarbon conversion processes are well known in the art and include cracking, hydrocracking, alkylation of aromatics or isoparaffins, isomerization of paraffin, olefins, or poly-alkylbenzene such as xylene, transalkylation of poly-alkybenzene with benzene or mono-alkybenzene, disproportionation of mono-alkybenzene, polymerization, reforming, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. No. 4,310,440 and U.S. Pat. No. 4,440,871 which are hereby incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of about 204° C. to about 649° C. (400° to 1200° F.) or about 316° C. to about 510° C. (600° F. and 950° F.). Reaction pressures are in the range of atmospheric to about 24,132 kPa g (3,500 psig), or between about 1379 to about 20,685 kPa g (200 to 3000 psig). Contact times usually correspond to liquid hourly space velocities (LHSV) in the range of about 0.1 hr$^{-1}$ to 15 hr$^{-1}$, preferably between about 0.2 and 3 hr$^{-1}$. Hydrogen circulation rates are in the range of 178 to about 8,888 std. m$^3$/m$^3$ (1,000 to 50,000 standard cubic feet (scf) per barrel of charge), or about 355 to about 5,333 std. m$^3$/m$^3$ (about 2,000 to about 30,000 scf per barrel of charge). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-39 composition using feedstocks such as gas oils, heavy naphthas, deasphalted crude oil residua, etc. with gasoline being the principal desired product. Temperature conditions of about 454° C. to about 593° C. (about 850° F. to about 1100° F.), LHSV values of 0.5 to 10 and pressure conditions of from about 0 to about 344 kPa g (about 0 to 50 psig) are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 1:1 and 30:1, a olefin LHSV of about 0.3 to about 10 $hr^{-1}$, a temperature of about 100° to about 250° C. and pressures of about 1379 kPa g to about 6895 kPa g (about 200 to about 1000 psig). Further details on apparatus may be found in U.S. Pat. No. 4,870,222 which is incorporated by reference.

Alkylation of isoparaffins with olefins to produce alkylates suitable as motor fuel components is carried out at temperatures of –30° to 40° C., pressures from about atmospheric to about 6,895 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The following examples are presented in illustration of this invention and are not intended as undue limitations on the generally broad scope of the invention as set out in the appended claims.

The structure of the UZM-39 zeolite of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

vw=<5; w=6-15; m=16-50: s=51-80; and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

EXAMPLE 1

A sample of UZM-39 was prepared as follows. 6.02 g of NaOH, (97%) was dissolved in 125.49 g water. 0.62 g Al(OH)$_3$, (29.32 wt.-% Al) was added to the NaOH solution to form a first solution. Separately, 0.24 g of the layered material UZM-8 was stirred into 30.0 g Ludox AS-40 to form a second solution. The second solution was added to the first solution. The mixture was cooled to 0° C.-4° C. Separately, 6.54 g 1,4-dibromobutane, (99 wt.-%) was mixed with 7.65 g 1-methylpyrrolidine, (97 wt.-%) to form a third solution. The third solution was added to the cooled mixture of the first and second solutions to form the final reaction mixture. The final reaction mixture was transferred to a 300 cc stirred autoclave and digested at 160° C. for 144 hours with stirring at 100 rpm. The product was isolated by filtration. The product was identified as UZM-39 by XRD as shown in FIG. 1. Analytical results show this material has the following molar rations: Si/Al of 12.64, Na/Al of 0.116, N/Al of 0.92, C/N of 7.23.

Figure 2:
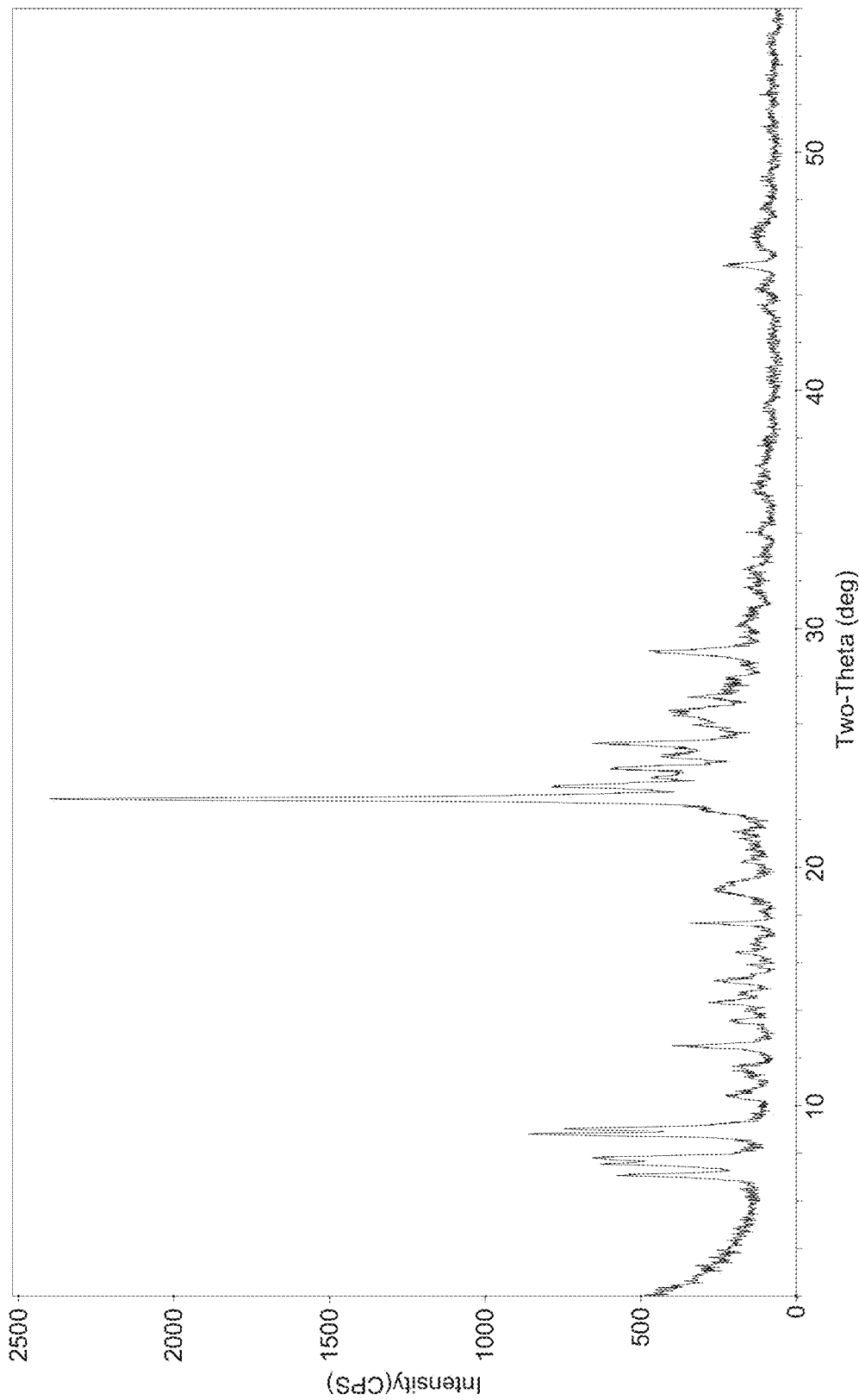
FIG. 2 is also an XRD pattern of the UZM-39 zeolite formed in Example 1. This pattern shows the UZM-39 zeolite after calcination.
Figure 7:
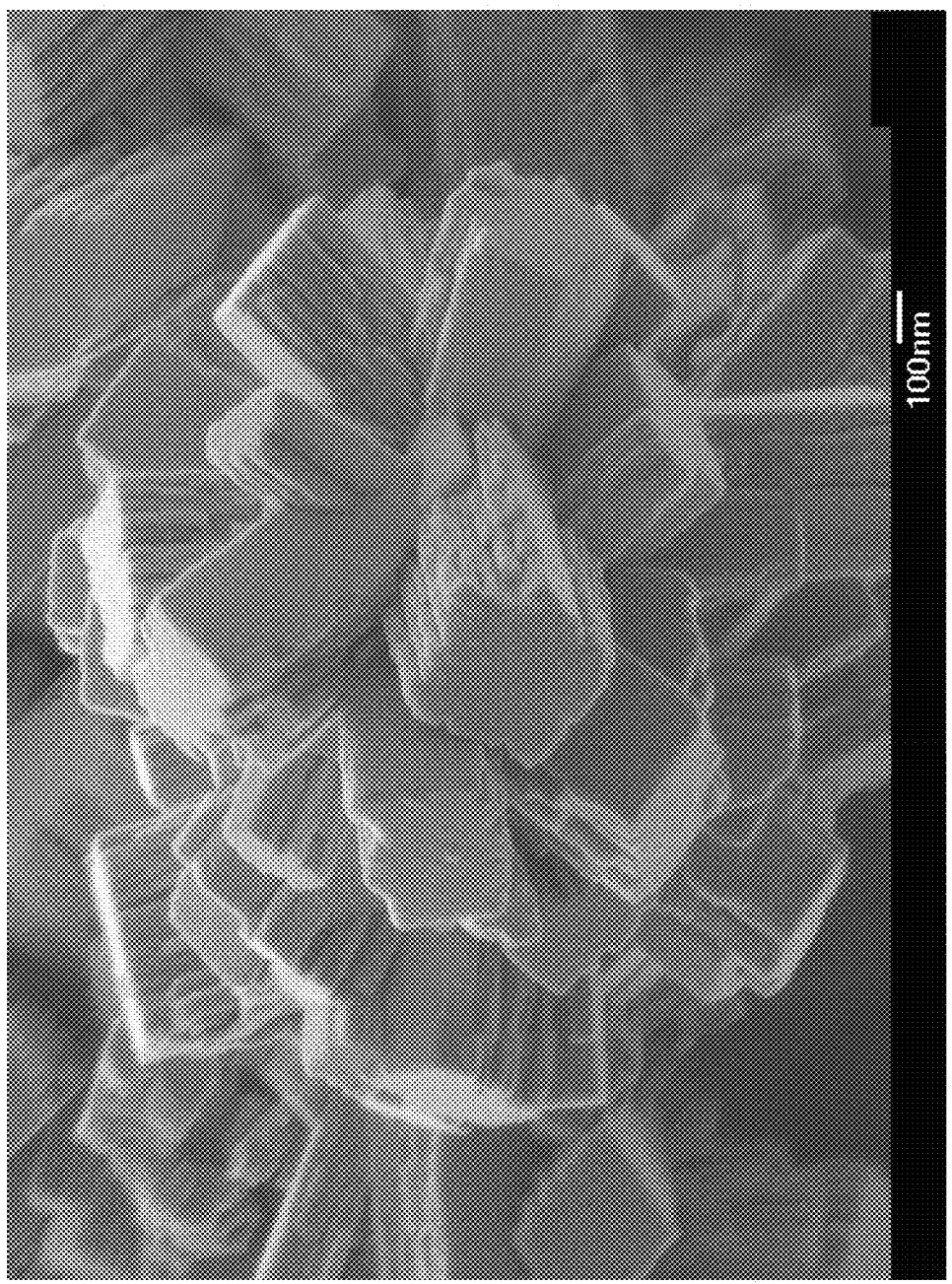
FIG. 7 shows the results of high-resolution scanning electron microscopy characterization of the UZM-39 product of Example 1. The electron micrograph shows that UZM-39 forms in lathes which assemble into rectangular rod particles, often with a starburst cluster arrangement. The starburst cluster rods of UZM-39 can be seen in the scanning electron microscopy results of FIG. 7.

Scanning Electron Microscopy (SEM) revealed crystals of intergrown, square rod morphology in starbursts, approximately 250 to 700 nm along a face of the square with an aspect ratio of from 2:1 to 5:1. The micrograph is shown in FIG. 7. The product was calcined at 550° C. for 3 hrs under air. The XRD pattern of the calcined material is shown in FIG. 2.

COMPARATIVE EXAMPLE 2

The preparation of Example 1 was followed, except that the layered material UZM-8 was not added to the second solution. After 144 hours of stirring at 100 rpm at 160° C., the product was isolated by filtration. The product was identified as analcime by XRD.

COMPARATIVE EXAMPLE 3

6.68 g of NaOH, (97%) was dissolved in 145.44 g water. 2.86 g Al(NO$_3$)$_3$.9H$_2$O (97%) was added to the sodium hydroxide solution. 13.33 g Aerosil 200 was stirred into the mixture. 13.1 g H$_2$O was added. 7.26 g 1,4-dibromobutane, (99%) and 5.84 g 1-methylpyrrolidine, (97%) were added and the mixture was stirred vigorously for a day. The mixture was divided equally and loaded into eight 45 cc Parr vessels and placed into a rotisserie oven at 160°. The mixture in one of the Parr vessels produced a material at 256 hours identified by XRD as having the TUN structure. Analytical results showed this material to have the following molar ratios, Si/Al of 15.51, Na/Al of 0.12, N/Al of 1.29, and C/N of 6.89. SEM analysis revealed a squat rod cluster morphology, about 300-800 nm in length and with an aspect ratio of about 1.

The product generated by this synthesis was calcined under flowing air at 600° for 6 hours. It was then ion exchanged four times with 1 M ammonium nitrate solution at 75° followed by a calcination at 500° under air for 2 hours to convert NH$_4^+$ into H$^+$.

Analysis for the calcined, ion-exchanged sample showed 39.2 wt. % Si, 2.34 wt. % Al, <0.005 wt. % Na with a BET surface area of 378 m$^2$/g, pore volume of 0.220 cm$^3$/g, and micropore volume of 0.190 cm$^3$/g.

Analysis of the H$^+$ form of this material by Rietveld XRD refinement showed that the material consisted entirely of TUN structure type. TEM analysis confirmed that no coherent growth of IMF crystals occurred.

EXAMPLE 4

6.40 g of NaOH, (97%) was dissolved in 111.88 g water. 1.16 g Al(OH)$_3$, (29.32 wt.-% Al), was added to the sodium hydroxide solution to create a first solution. Separately, 0.30 g of the layered material (UZM-8) was stirred into 37.5 g Ludox AS-40 to form a second solution. The second solution was added to the first solution and vigorously stirred for 1-2 hours. The mixture was cooled to 0° C.-4° C. Separately, 8.18 g 1,4-dibromobutane, (99 wt.-%) was mixed with 9.56 g 1-methylpyrrolidine, (97 wt.-%) to form a third solution. The third solution was added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 by XRD. Analytical results showed this material to have the following molar ratios, Si/Al of 12.07, Na/Al of 0.124, N/Al of 0.90, C/N of 6.85.

EXAMPLE 5

7.19 g of NaOH, (99 wt.-%%) was dissolved in 90.1 g water. 1.56 g Al(OH)$_3$, (29.32 wt.-% Al), was added to the sodium hydroxide solution to create a first solution. Separately, 0.405 g of the layered material (UZM-8) was stirred into 50.62 g Ludox AS-40 to form a second solution. The second solution was added to the first solution and vigorously stirred for 1-2 hours. The mixture was cooled to 0° C.-4° C. Separately, 11.04 g 1,4-dibromobutane, (99 wt.-%), was mixed with 12.90 g 1-methylpyrrolidine, (97 wt.-%) to form a third solution. The third solution was added to the cooled mixture to create the final reaction mixture. The final reaction mixture was vigorously stirred for 5 minutes and transferred to a 300 cc stirred autoclave. The final reaction mixture was digested at 160° C. for 144 hours with stirring at 100 rpm. 16.5 g of the product was isolated by filtration. The product was identified by XRD to be UZM-39 with a very slight MOR impurity. Analytical results showed this material to have the following molar ratios, Si/Al of 14.14, Na/Al of 0.16, N/Al of 1.02, C/N of 7.33.

EXAMPLE 6

37.62 g of NaOH, (97 wt.-%) was dissolved in 600 g water to create a sodium hydroxide solution. 6.96 g Al(OH)$_3$ (29.32 mass % Al) was added to the sodium hydroxide solution to create a first solution. Separately, 1.80 g of the layered material (UZM-8) was stirred into 225 g Ludox AS-40 to form a second solution. The second solution was added to the first solution and vigorously stirred for 1-2 hours. The mixture was cooled to 0° C.-4° C. Separately, 49.08 g 1,4-dibromobutane (99 wt.-%) was mixed with 57.36 g 1-methylpyrrolidine (97 wt.-%) for 1-5 minutes to form a third solution. The third solution was added to the cooled mixture to create the final reaction mixture. The final reaction mixture was vigorously stirred for 5 minutes and transferred to a 2 liter stirred autoclave. The final reaction mixture was digested at 160° C. for 144 hours with stirring at 250 rpm. The product was isolated by filtration. The product was identified by XRD as UZM-39. Analytical results showed this material to have the following molar ratios, Si/Al of 11.62, Na/Al of 0.12, N/Al of 0.88, C/N of 7.36.

The product generated by this synthesis was calcined under flowing air at 600° for 6 hours. It was then ion exchanged four times with 1 M ammonium nitrate solution at 75° followed by a calcination at 500° C. under air for 2 hours to convert NH$_4^+$ into H$^+$. Analysis of the H$^+$ form of this material by Rietveld XRD refinement gave the results shown in Table 1.

EXAMPLE 7

505.68 g of NaOH, (99 wt.-%) was dissolved in 10542 g water. 52.08 g Al(OH)$_3$, (29.3 wt.-% Al), was added to the sodium hydroxide solution to create a first solution. Separately, 20.16 g of the layered material (UZM-8) was stirred into 2520 g Ludox AS-40 to form a second solution. The second solution was added to the first solution and vigorously stirred for 1-2 hours. The mixture was cooled to 0° C.-4° C. Separately, 549.36 g 1,4-dibromobutane (99 wt.-%) was mixed with 642.6 g 1-methylpyrrolidine, (97 wt.-%), for 3-5 minutes to form a third solution. The third solution was added to the cooled mixture to create the final reaction mixture. The final reaction mixture was vigorously stirred for 5 minutes and pumped into a 5 gallon stirred autoclave. The final reaction mixture was digested at 160° C. for 150 hours with stirring at 100 rpm. The product was isolated by filtration. The product was identified by XRD as UZM-39. Analytical results showed this material to have the following molar ratios, Si/Al=13.35, Na/Al=0.087, N/Al=0.96, C/N=7.12.

EXAMPLE 8

The preparation of Example 4 was followed except that UZM-8 was replaced with 0.30 g UZM-26. The product was identified by XRD as UZM-39. Analytical results showed this material to have the following molar ratios: Si/Al=12.88, Na/Al=0.25, N/Al=0.88, C/N=7.31.

EXAMPLE 9

6.27 g of NaOH, (99%), was dissolved in 111.88 g water to create a sodium hydroxide solution. 1.16 g Al(OH)$_3$ (29.32 mass % Al) was added to the sodium hydroxide solution to create a first solution. 37.5 g Ludox AS-40 and then 0.22 g of the layered material UZM-5 were added to the first solution. The first solution was vigorously stirred for 1-2 hours. The first solution was cooled to 0° C.-4° C. Separately, 8.18 g 1,4-dibromobutane (99%) was mixed with 9.56 g 1-methylpyrrolidine (97%) for 1-5 minutes to form a second solution. The second solution was added to the cooled first solution to create the final reaction mixture. The final reaction mixture was vigorously stirred for approximately 5 minutes and transferred to a 300 cc stirred autoclave. The final reaction mixture was digested at 160° C. for 144 hours with stirring at 100 rpm. The product was isolated by filtration. The product was identified by XRD as UZM-39 with a very small EUO or NES contaminant.

COMPARATIVE EXAMPLE 10

This example is identical to example 4 except that UZM-8 was replaced with 0.30 g UZM-39. The product was identified as a composition comprising MTW, UZM-39, ANA and MOR.

EXAMPLE 11

6.27 g of NaOH, (97 wt.-%) was dissolved in 111.88 g water. 1.16 g Al(OH)$_3$, (29.32 wt. % Al), was added to the sodium hydroxide solution to create a first solution. Separately, 0.30 g of the layered material (UZM-8) was stirred into 37.5 g Ludox AS-40 to form a second solution. The second solution was added to the first solution and vigorously stirred for 1-2 hours. The mixture was cooled to 0° C.-4° C. Separately, 12.27 g 1,4-dibromobutane (99 wt.-%) was mixed with 14.34 g 1-methylpyrrolidine (97 wt.-%) to form a third solution. The third solution was added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 with an ESV impurity by XRD. Analytical results showed this material to have the following molar ratios, Si/Al=13.17, Na/Al=0.126, N/Al=1.03, C/N=7.22.

EXAMPLE 12

The procedure of Example 4 was followed except 9.56 g 1-methylpyrrolidine, (97 wt.-%), was replaced with 8.05 g dimethylethylamine, (97 wt.-%). The product was identified as a composition comprising mordenite and UZM-39.

EXAMPLE 13

6.27 g of NaOH (99 wt.-%) was dissolved in 111.88 g water 1.16 g Al(OH)$_3$ (29.32 wt.-% Al) was added to the sodium hydroxide solution to create a first solution. 0.30 g of the layered material UZM-8 and 37.5 g Ludox AS-40 were added to the first solution. The first solution was vigorously stirred for 1-2 hours. The first solution was cooled to 0° C.-4° C. Separately, 4.02 g dimethylethylamine (97 wt.-%) was mixed with 4.78 g 1-methylpyrrolidine (97 wt.-%) for 1-2 minutes to form an amine solution. 8.18 g 1,4-dibromobutane (99 wt.-%) was added to the amine solution and then mixed for 1-2 minutes to form a second solution. The second solution was added to the cooled first solution to create the final reaction mixture. The final reaction mixture was vigorously stirred for approximately 5 minutes and transferred to a 300 cc stirred autoclave. The final reaction mixture was digested at 160° C. for 192 hours with stirring at 100 rpm. The product was isolated by filtration. The product was identified as UZM-39 by XRD. Analytical results showed this material to have the following molar ratios, Si/Al=12.42, Na/Al=0.175, N/Al=0.91, C/N=6.92.

The product generated by this synthesis was calcined under flowing air at 600° for 6 hours. It was then ion exchanged four times with 1 M ammonium nitrate solution at 75° followed by a calcination at 500° C. under air for 2 hours to convert NH$_4^+$ into H$^+$. Analysis for the calcined, ion-exchanged sample shows 38.7% Si, 2.97% Al, 0.0089% Na with a BET surface area of 375 m$^2$/g, pore volume of 0.238 cm$^3$/g, and micropore volume of 0.184 cm$^3$/g. Analysis of the H$^+$ form of this material by Rietveld XRD refinement gave the results shown in Table 1.

EXAMPLE 14

6.21 g of NaOH, (99%), was dissolved in 111.88 g water to create a sodium hydroxide solution. 1.16 g Al(OH)$_3$ (29.32 wt.-% Al) was added to the sodium hydroxide solution to create a first solution. 0.30 g of the layered material (UZM-8) and 37.5 g Ludox AS-40 were added to the first solution. The first solution was vigorously stirred for 1-2 hours. The first solution was cooled to 0° C.-4° C. Separately, 8.18 g 1,4-dibromobutane (99 wt.-%) was mixed with 9.56 g 1-methylpyrrolidine (97 wt.-%) for 1-5 minutes to form a second solution. The second solution was added to the cooled first solution to create the final reaction mixture. The final reaction mixture was vigorously stirred for approximately 5 minutes and transferred to a 300 cc stirred autoclave. The final reaction mixture was digested at 170° C. for 96 hours with stirring at 100 rpm. The product was isolated by filtration. The product was identified as UZM-39 by XRD. Analytical results showed this material to have the following molar ratios, Si/Al of 12.76, Na/Al of 0.116, N/Al of 0.94, C/N of 6.98.

EXAMPLE 15

6.21 g of NaOH, (99%), was dissolved in 111.88 g water to create a sodium hydroxide solution. 1.16 g Al(OH)$_3$ (29.32 wt.-% Al) was added to the sodium hydroxide solution to create a first solution. 0.30 g of the layered material (UZM-8) and 37.5 g Ludox AS-40 were added to the first solution. The first solution was vigorously stirred for 1-2 hours. The first solution was cooled to 0° C.-4° C. Separately, 8.18 g 1,4-dibromobutane (99 wt.-%) was mixed with 9.56 g 1-methylpyrrolidine (97 wt.-%) for 1-5 minutes to form a second solution. The second solution was added to the cooled first solution to create the final reaction mixture. The final reaction mixture was vigorously stirred for approximately 5 minutes and transferred to a 300 cc stirred autoclave. The final reaction mixture was digested at 175° C. for 44 hours with stirring at 100 rpm. The product was isolated by filtration. The product was identified as UZM-39 by XRD. Analytical results showed this material to have the following molar ratios, Si/Al of 12.97, Na/Al of 0.20, N/Al of 0.95, C/N of 6.98.

EXAMPLE 16

5.96 g of NaOH, (97%) and 0.25 g KOH, (86%) were dissolved in 111.88 g water. 1.22 g Al(OH)$_3$, (27.9 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave.

The final reaction mixture was digested at 160° C. for 144 hours with stirring at 100 rpm. The product was isolated by filtration. The product was identified as UZM-39 by XRD. The x-ray diffraction pattern is shown in FIG. 3. Analytical results showed this material to have the following molar ratios, Si/Al of 11.69, Na/Al of 0.137, K/Al of 0.024, N/Al of 0.848, C/N of 7.16.

Figure 4:
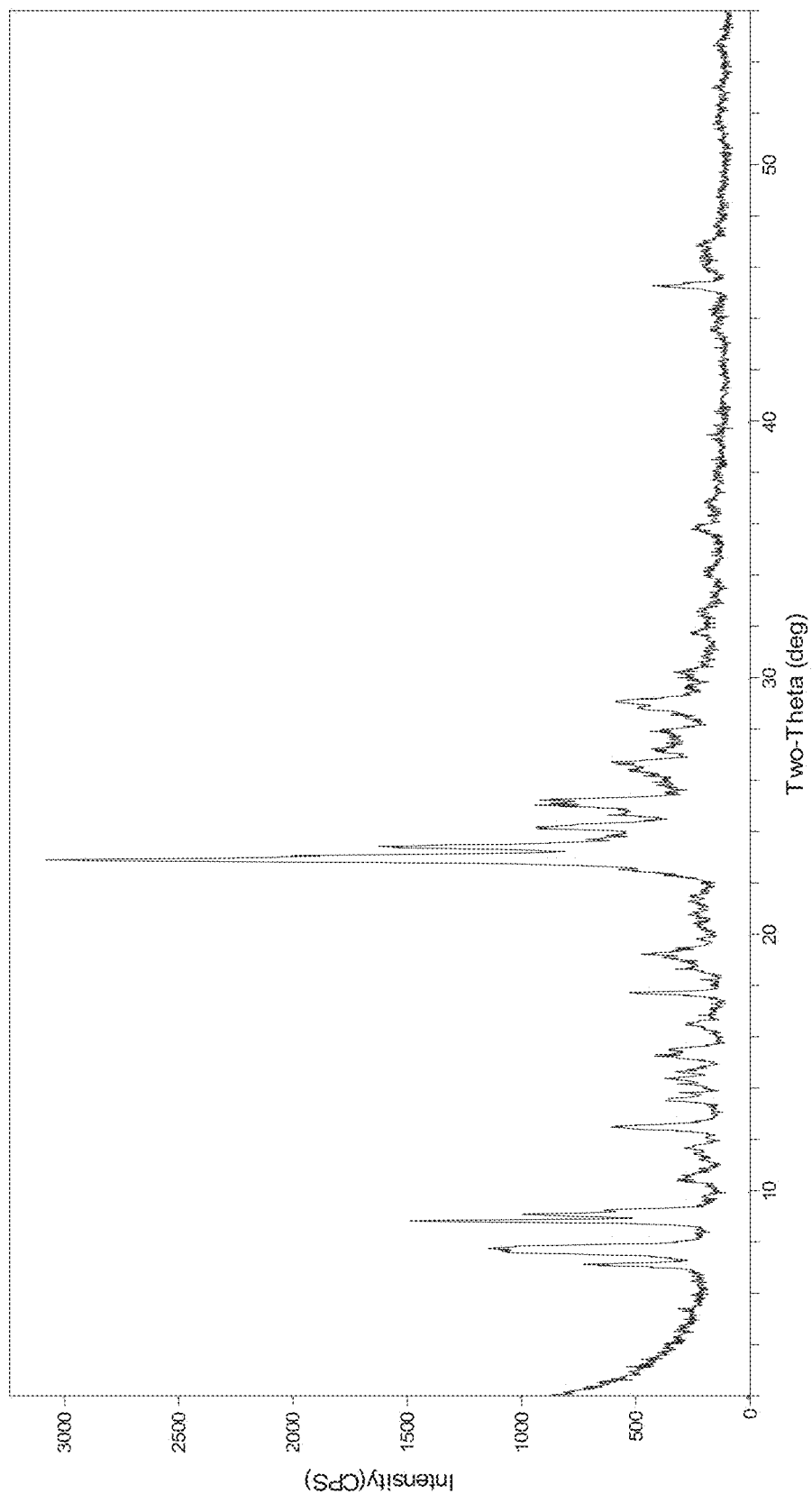
FIG. 4 is also an XRD pattern of the UZM-39 zeolite formed in Example 16. This pattern shows the UZM-39 zeolite in the H$^+$ form.

The product generated by this synthesis was calcined under flowing air at 600° for 6 hours. It was then ion exchanged four times with 1 M ammonium nitrate solution at 75° followed by a calcination at 500° C. under air for 2 hours to convert NH$_4^+$ into Ft. Analysis for the calcined, ion-exchanged sample shows 39.4% Si, 3.23% Al, 0.011% Na, 0.005% K with a BET surface area of 362 m$^2$/g, pore volume of 0.231 cm$^3$/g, and micropore volume of 0.176 cm$^3$/g. The x-ray diffraction pattern in shown in FIG. 4.

EXAMPLE 17

5.96 g of NaOH, (99%) and 0.50 g KOH, (86%) were dissolved in 111.88 g water. 1.16 g Al(OH)$_3$, (29.32 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 4.09 g 1,4-dibromobutane, (99%) was mixed with 11.15 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 by XRD. Analytical results showed this material to have the following molar ratios, Si/Al of 11.98, Na/Al of 0.114, K/Al of 0.0375 N/Al of 0.84, C/N of 7.50.

Figure 11:
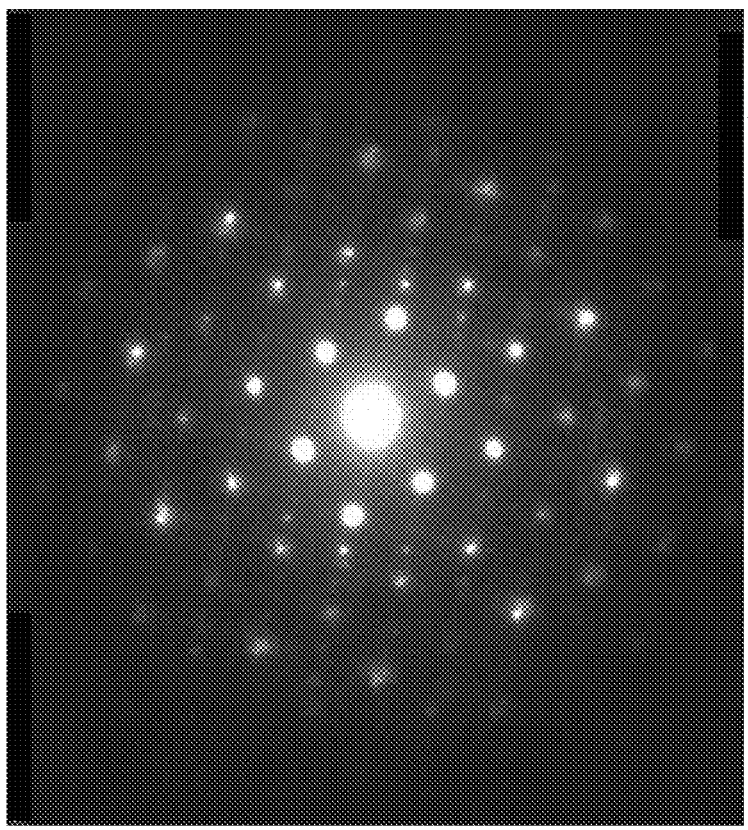
FIG. 11 is an electron diffraction analysis of the cross sectioned rod particle of FIG. 10 and shows that from what appears to be a single-crystalline zeolite particle, areas that index to [010] zone axis of TUN and to [001] zone axis of IMF are found. The TUN regions and IMF regions are coherently aligned.
Figure 11:
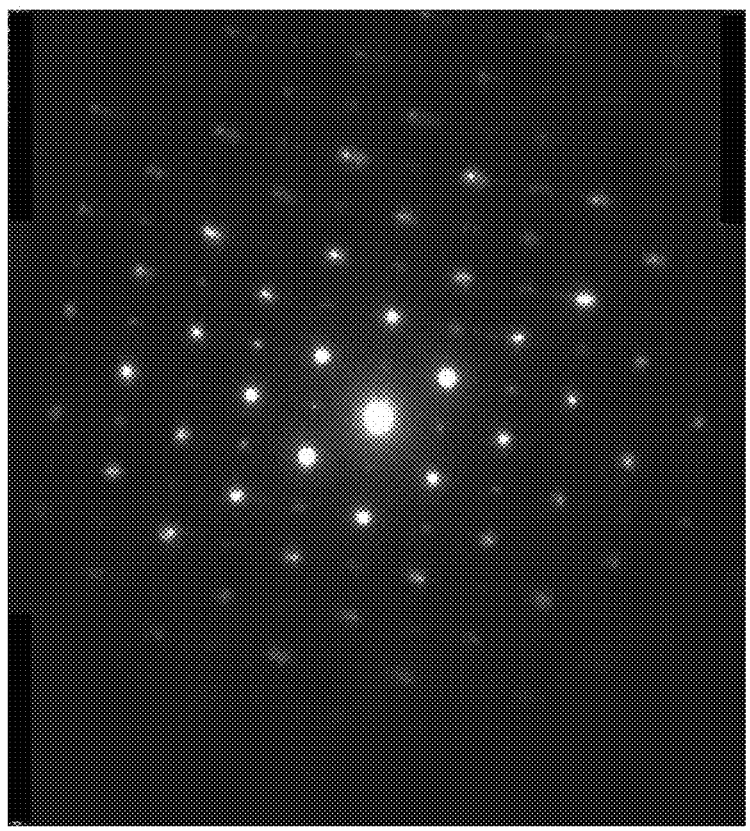

The product generated by this synthesis was calcined under flowing air at 600° for 6 hours. It was then ion exchanged four times with 1 M ammonium nitrate solution at 75° followed by a calcination at 500° C. under air for 2 hours to convert $NH_4^+$ into Ft. Analysis for the calcined, ion-exchanged sample shows 37.7% Si, 3.01% Al, 0.012% Na, 0.006% K. Analysis of the $H^+$ form of this material by Rietveld XRD refinement gave the results shown in Table 1. TEM analysis showed that UZM-39 is a coherently grown composite structure of TUN and IMF zeotypes, the results of which analysis are shown in FIGS. 10 and 11.

EXAMPLE 18

Figure 8:
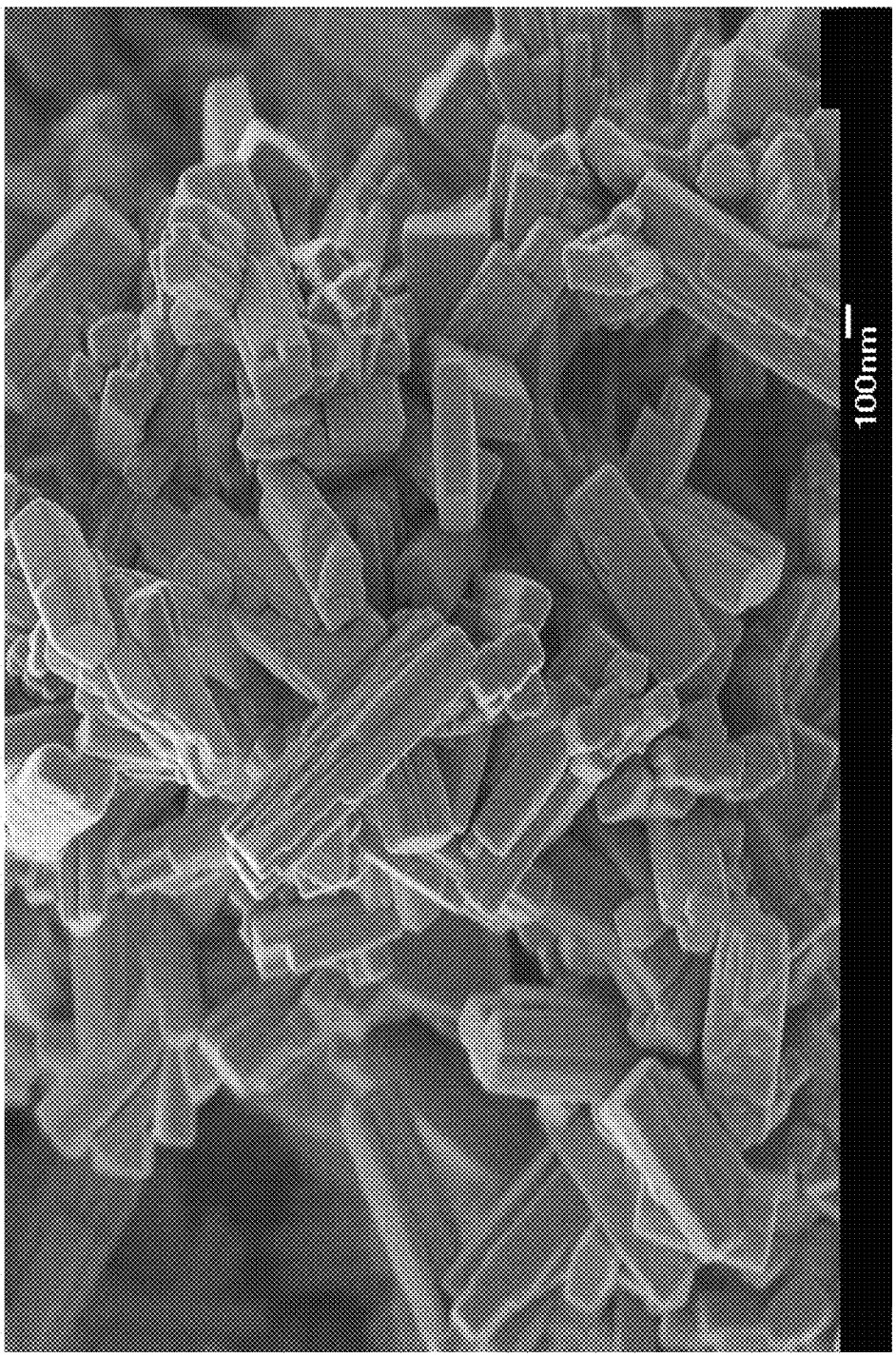
FIG. 8 shows the results of high-resolution scanning electron microscopy characterization of a different UZM-39, that of the product of Example 18. The electron micrograph also shows lathes assembled into rectangular rod particles with a number of starburst cluster arrangements.

5.64 g of NaOH, (97%) and 1.00 g KOH, (86%) were dissolved in 111.88 g water. 1.22 g $Al(OH)_3$, (27.9 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 by XRD. Analytical results showed this material to have the following molar ratios, Si/Al of 11.29, Na/Al of 0.078, K/Al of 0.053 N/Al of 0.88, C/N of 6.92. The SEM image of the product is shown in FIG. 8.

The product generated by this synthesis was calcined under flowing air at 600° for 6 hours. It was then ion exchanged four times with 1 M ammonium nitrate solution at 75° followed by a calcination at 500° C. under air for 2 hours to convert $NH_4^+$ into $H^+$. Analysis for the calcined, ion-exchanged sample shows 42.6% Si, 3.65% Al, 0.0018% Na, 0.02% K with a BET surface area of 351 $m^2/g$, pore volume of 0.218 $cm^3/g$, and micropore volume of 0.170 $cm^3/g$. Analysis of the $H^+$ form of this material by Rietveld XRD refinement gave the results shown in Table 1.

EXAMPLE 19

5.02 g of NaOH, (97%) and 2.00 g KOH, (86%) were dissolved in 111.88 g water. 1.22 g $Al(OH)_3$, (27.9 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 136 hours with stirring at 100 rpm. The product was isolated by filtration. The product was identified as UZM-39 by XRD with a likely small amount of NES contaminant Analytical results showed this material to have the following molar ratios, Si/Al of 10.99, Na/Al of 0.088, K/Al of 0.11 N/Al of 0.84, C/N of 7.36.

EXAMPLE 20

5.96 g of NaOH, (99%) was dissolved in 111.88 g water. 1.22 g $Al(OH)_3$, (27.9 wt.-% Al), was added to the sodium hydroxide solution. Then 0.24 g $Mg(OH)_2$ (95%), 37.5 g Ludox AS-40, and 0.30 g of the layered material UZM-8 were added in the order listed to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) and added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 by XRD. Analytical results showed this material to have the following molar ratios, Si/Al of 12.12, Na/Al of 0.148, Mg/Al of 0.38 N/Al of 0.91, C/N of 6.96.

The product generated by this synthesis was calcined under flowing air at 600° for 6 hours. It was then ion exchanged four times with 1 M ammonium nitrate solution at 75° followed by a calcination at 500° C. under air for 2 hours to convert $NH_4^+$ into $H^+$. Analysis for the calcined, ion-exchanged sample shows 39.6% Si, 2.99% Al, 83 ppm Na, 0.14% Mg with a BET surface area of 351 $m^2/g$, pore volume of 0.218 $cm^3/g$, and micropore volume of 0.170 $cm^3/g$.

EXAMPLE 21

5.96 g of NaOH, (99%) and 0.51 g $La(OH)_3$, (99.9%) were dissolved in 111.88 g water. 1.16 g $Al(OH)_3$, (29.32 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) and added to the cooled mixture to create the final reaction mixture. The final reaction mixture was vigorously stirred and transferred to a 300 cc stirred autoclave. The final reaction mixture was digested at 160° C. for 168 hours with stirring at 100 rpm. The product was isolated by filtration. The product was identified as UZM-39 by XRD. Analytical results showed this material to have the following molar ratios, Si/Al of 12.22, Na/Al of 0.20, La/Al of 0.18, N/Al of 0.89, C/N of 7.13.

The product generated by this synthesis was calcined under flowing air at 600° for 6 hours. It was then ion exchanged four times with 1 M ammonium nitrate solution at 75° followed by a calcination at 500° C. under air for 2 hours to convert $NH_4^+$ into $H^+$. Analysis for the calcined, ion-exchanged sample shows 39.1% Si, 3.06% Al, 60 ppm Na, 0.25% La with a BET surface area of 335 $m^2/g$, pore volume of 0.226 $cm^3/g$, and micropore volume of 0.163 $cm^3/g$.

EXAMPLE 22

3.14 g of NaOH, (97%) was dissolved in 106.41 g water. 1.16 g $Al(OH)_3$, (29.32 wt.-% Al), was added to the sodium hydroxide solution. 37.5 g Ludox AS-40 and then 0.30 g of the layered material UZM-8 were added to the first solution. Next 26.7 g Na silicate solution (13.2 wt. % Si; 6.76 wt. % Na) is added to the above and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 224 hours with stirring at 100 rpm. The product was isolated by filtration. The product was identified as UZM-39 by XRD. Analytical results showed this material to have the following molar ratios, Si/Al of 11.75, Na/Al of 0.11, N/Al of 0.90, C/N of 6.99.

The product generated by this synthesis was calcined under flowing air at 600° for 6 hours. It was then ion exchanged three times with 1 M ammonium nitrate solution at 75° followed by a calcination at 500° C. under air for 2 hours to convert $NH_4^+$ into $H^+$. Analysis for the calcined, ion-exchanged sample shows 38.8% Si, 3.05% Al, 0.011% Na, with a BET surface area of 364 $m^2/g$, pore volume of 0.273 $cm^3/g$, and micropore volume of 0.174 $cm^3/g$. Analysis of the $H^+$ form of this material by Rietveld XRD refinement gave the results shown in Table 1.

EXAMPLE 23

5.33 g of NaOH, (99%) was dissolved in 111.88 g water. 1.16 g $Al(OH)_3$, (29.32 wt.-% Al), was added to the sodium hydroxide solution. Separately, 0.30 g of Beta zeolite was stirred into 37.5 g Ludox AS-40 to make a second mixture. This second mixture was added to the first solution and stirred vigorously for 1-2 hours. The mixture was cooled to 0° C.-4° C. Separately, 8.89 g 1,5-dibromopentane, (97%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 256 hours with stirring at 100 rpm. The product was isolated by filtration. The product was identified as UZM-39 by XRD. Analytical results showed this material to have the following molar ratios, Si/Al of 13.24, Na/Al of 0.13, N/Al of 0.91, C/N of 7.21.

The product generated by this synthesis was calcined under flowing air at 600° for 6 hours. It was then ion exchanged three times with 1 M ammonium nitrate solution at 75° followed by a calcination at 500° C. under air for 2 hours to convert $NH_4^+$ into Ft. Analysis of the $H^+$ form of this material by Rietveld XRD refinement gave the results shown in Table 1.

COMPARATIVE EXAMPLE 24

10.8 g of Aerosil 200 was added, while stirring, to a solution of 12.24 g 1,5-bis(N-methylpyrrolidinium)pentane dibromide in 114 g $H_2O$. A very thick gel was formed. Separately, a solution was made from 60 g $H_2O$, 3.69 g NaOH (99%), 0.95 g sodium aluminate (26.1% Al by analysis), and 1.86 g NaBr (99%). This second solution was added to the above mixture which thins out a bit. The final mixture was divided equally between 7 45 cc Parr vessels. One vessel, which was digested for 12 days at 170° C. in a rotisserie oven at 15 rpm, yielded a product which was determined by XRD as having the IMF structure. The product was isolated by filtration. The product generated by this synthesis was calcined under flowing air at 600° for 6 hours. It was then ion exchanged four times with 1 M ammonium nitrate solution at 75° followed by a calcination at 500° under air for 2 hours to convert $NH_4^+$ into $H^+$. Analysis of the H+-form of this material by Rietveld XRD refinement showed that the material consisted entirely of IMF structure type. TEM analysis confirmed that no coherent growth of TUN crystals occurred.

EXAMPLE 25

31.98 g of NaOH, (99%) was dissolved in 671.3 g water. 6.96 g $Al(OH)_3$, (29.32 wt.-% Al), was added to the sodium hydroxide solution. Separately, 1.80 g of the layered material UZM-8 was stirred into 225.0 g Ludox AS-40 to make a second mixture. This second mixture was added to the first solution and stirred vigorously for 1-2 hours. The mixture was cooled to 0° C.-4° C. Separately, 53.34 g 1,5-dibromopentane, (97%) was mixed with 57.36 g 1-methylpyrrolidine, (97%) to form a third mixture. The third mixture was added to the cooled mixture to create the final reaction mixture. The final reaction mixture was vigorously stirred and transferred to a 2 L stirred autoclave. The final reaction mixture was digested at 160° C. for 256 hours with stirring at 250 rpm. The product was isolated by filtration. The product was identified as UZM-39 by XRD. Analytical results showed this material to have the following molar ratios, Si/Al of 12.30, Na/Al of 0.13, N/Al of 0.92, C/N of 7.51.

The product generated by this synthesis was calcined under flowing air at 600° C. for 6 hours. It was then ion exchanged three times with 1 M ammonium nitrate solution at 75° C. followed by a calcination at 500° C. under air for 2 hours to convert $NH_4^+$ into $H^+$. Analysis for the calcined, ion-exchanged sample shows 39.0% Si, 2.93% Al, 0.008% Na. Analysis of the $H^+$ form of this material by Rietveld XRD refinement gave the results shown in Table 1.

EXAMPLE 26

5.76 g of NaOH, (97%) was dissolved in 111.88 g water. 1.22 g $Al(OH)_3$, (27.9 wt.-% Al), was added to the sodium hydroxide solution. When this became a solution, 37.5 g Ludox AS-40 was added. Next 0.30 g of the layered material UZM-8 was added. The mixture was stirred vigorously for 1-2 hours. The mixture was cooled to 0° C.-4° C. Separately, 0.89 g 1,5-dibromopentane, (97%) was mixed with 7.36 g 1,4-dibromobutane, (99%), then 9.56 g 1-methylpyrrolidine, (97%) was added to form a second mixture. The second mixture was added to the cooled mixture to create the final reaction mixture. The final reaction mixture was vigorously stirred and transferred to a 300 cc stirred autoclave. The final reaction mixture was digested at 160° C. for 176 hours with stirring at 100 rpm. The product was isolated by filtration. The product was identified as UZM-39 by XRD. Analytical results showed this material to have the following molar ratios, Si/Al of 12.15, Na/Al of 0.15, N/Al of 0.90, C/N of 7.59.

The product generated by this synthesis was calcined under flowing air at 600° C. for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 38.6% Si, 2.85% Al, <0.01% Na. Analysis of the $H^+$ form of this material by Rietveld XRD refinement gave the results shown in Table 1.

EXAMPLE 27

5.76 g of NaOH, (97%) was dissolved in 111.88 g water. 1.22 g $Al(OH)_3$, (27.9 wt.-% Al), was added to the sodium hydroxide solution. When this became a solution, 37.5 g Ludox AS-40 was added. Next, 0.30 g of the layered material UZM-8 was added and the mixture was stirred vigorously for 1-2 hours. The mixture was cooled to 0° C.-4° C. Separately, 1.78 g 1,5-dibromopentane, (97%) was mixed with 6.54 g 1,4-dibromobutane, (99%), then 9.56 g 1-methylpyrrolidine, (97%) was added to form a second mixture. The second mixture was added to the cooled mixture to create the final reaction mixture. The final reaction mixture was vigorously stirred and transferred to a 300 cc stirred autoclave. The final reaction mixture was digested at 160° C. for 176 hours with stirring at 100 rpm. The product was isolated by filtration. The product was identified as UZM-39 by XRD. Analytical results showed this material to have the following molar ratios, Si/Al of 12.24, Na/Al of 0.107, N/Al of 0.93, C/N of 6.91.

The product generated by this synthesis was calcined under flowing air at 600° C. for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 38.7% Si, 2.98% Al, 158 ppm Na with a BET surface area of 333 $m^2/g$, pore volume of 0.201 $cm^3/g$, and micropore volume of 0.164 $cm^3/g$. Analysis of the $H^+$ form of this material by Rietveld XRD refinement gave the results shown in Table 1

EXAMPLE 28

5.76 g of NaOH, (97%) was dissolved in 111.88 g water. 1.22 g $Al(OH)_3$, (27.9 wt.-% Al), was added to the sodium hydroxide solution. When this became a solution, 37.5 g Ludox AS-40 was added. Next, 0.30 g of the layered material UZM-8 was added and the mixture was stirred vigorously for 1-2 hours. The mixture was cooled to 0° C.-4° C. Separately, 2.67 g 1,5-dibromopentane, (97%) was mixed with 5.73 g 1,4-dibromobutane, (99%), then 9.56 g 1-methylpyrrolidine, (97%) was added to form a second mixture. The second mixture was added to the cooled mixture to create the final reaction mixture. The final reaction mixture was vigorously stirred and transferred to a 300 cc stirred autoclave. The final reaction mixture was digested at 160° C. for 176 hours with stirring at 100 rpm. The product was isolated by filtration. The product was identified as UZM-39 by XRD; the pattern is shown in FIG. 5. Analytical results showed this material to have the following molar ratios, Si/Al of 12.15, Na/Al of 0.108, N/Al of 0.86, C/N of 7.68.

Figure 6:
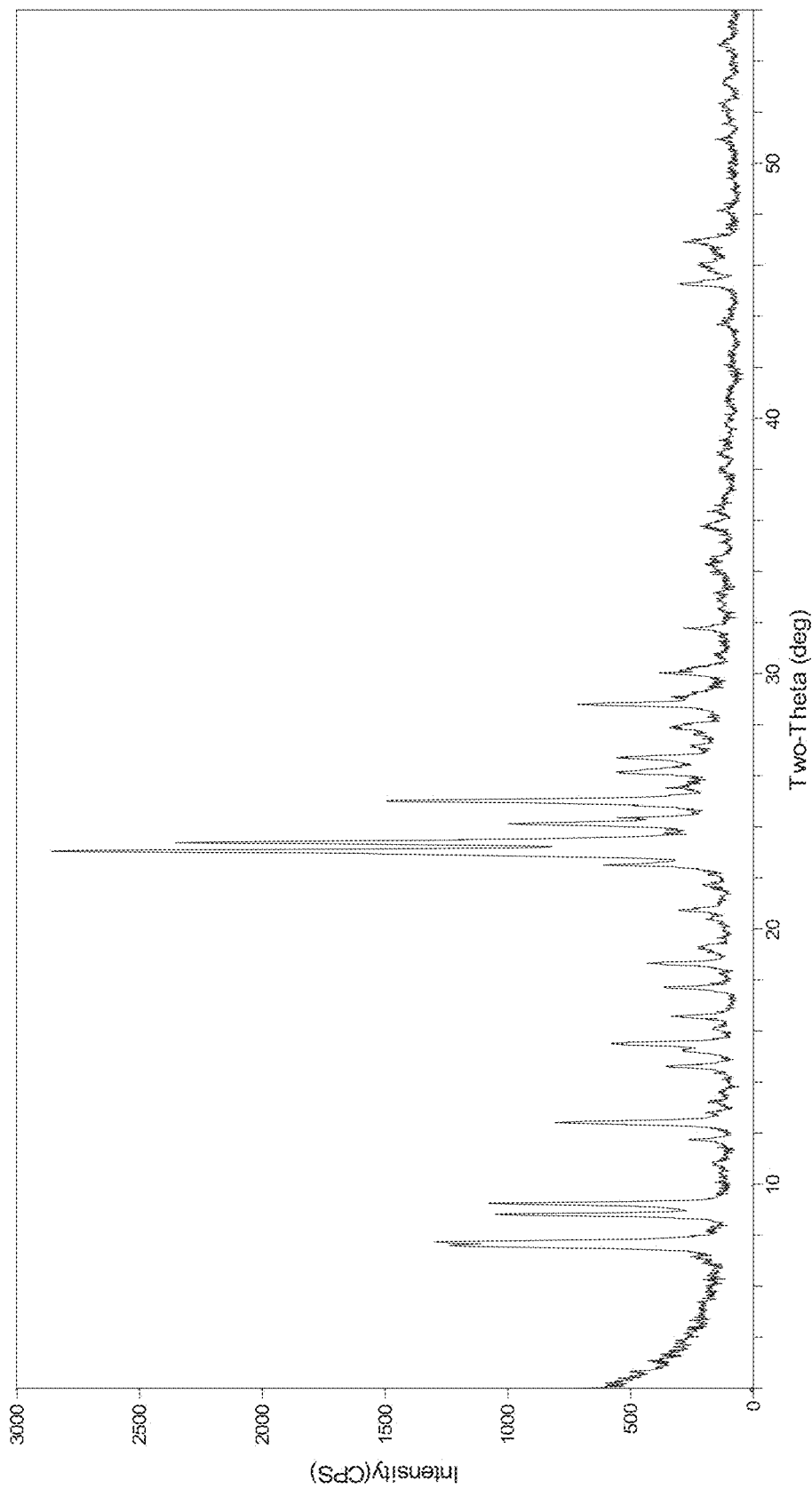
FIG. 6 is also an XRD pattern of the UZM-39 zeolite formed in Example 28. This pattern shows the UZM-39 zeolite in the H$^+$ form.

The product generated by this synthesis was calcined under flowing air at 600° C. for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 38.7% Si, 2.98% Al, 79 ppm Na. The x-ray diffraction pattern is shown in FIG. 6. Analysis of the $H^+$ form of this material by Rietveld XRD refinement gave the results shown in Table 1.

EXAMPLE 29

5.80 g of NaOH, (97%) was dissolved in 111.88 g water. 1.16 g $Al(OH)_3$, (29.32 wt.-% Al), was added to the sodium hydroxide solution. When this became a solution, 37.5 g Ludox AS-40 was added. Next, 0.30 g of the layered material UZM-8 was added and the mixture was stirred vigorously for 1-2 hours. The mixture was cooled to 0° C.-4° C. Separately, 4.45 g 1,5-dibromopentane, (97%) was mixed with 4.09 g 1,4-dibromobutane, (99%), then 9.56 g 1-methylpyrrolidine, (97%) was added to form a second mixture. The second mixture was added to the cooled mixture to create the final reaction mixture. The final reaction mixture was vigorously stirred and transferred to a 300 cc stirred autoclave. The final reaction mixture was digested at 160° C. for 224 hours with stirring at 100 rpm. The product was isolated by filtration. The product was identified as UZM-39 by XRD. Analytical results showed this material to have the following molar ratios, Si/Al of 11.75, Na/Al of 0.13, N/Al of 0.86, C/N of 7.59.

The product generated by this synthesis was calcined under flowing air at 600° C. for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 40.1% Si, 3.32% Al, 90 ppm Na with a BET surface area of 305 $m^2/g$, pore volume of 0.224 $cm^3/g$, and micropore volume of 0.146 $cm^3/g$. Analysis of the $H^+$ form of this material by Rietveld XRD refinement gave the results shown in Table 1.

TABLE 1

| Example # | % TUN | % IMF |
|---|---|---|
| 3 | 100 | 0 |
| 6 | 95 | 5 |
| 13 | 83 | 17 |
| 17 | 46 | 54 |
| 18 | 36.5 | 63.5 |
| 23 | 24 | 76 |
| 24 | 0 | 100 |
| 25 | 19 | 81 |
| 26 | 58 | 42 |
| 27 | 30 | 70 |
| 28 | 13 | 87 |
| 29 | 8 | 92 |

EXAMPLE 30

To determine the quantities of TUN or IMF structure able to be detected in a UZM-39 coherently grown composite structure material, a detection limit study was performed. A series of simulated diffraction patterns were electronically created from the observed diffraction patterns of the $H^+$ forms of Example 3 and Example 24 products using JADE XRD analysis software (available from Materials Data Incorporated). Mixture levels ranged from 1% to 99% TUN and were created by scaling the smaller percentage constituent to the required level, adding the patterns and saving the composite pattern.

Figure 12:
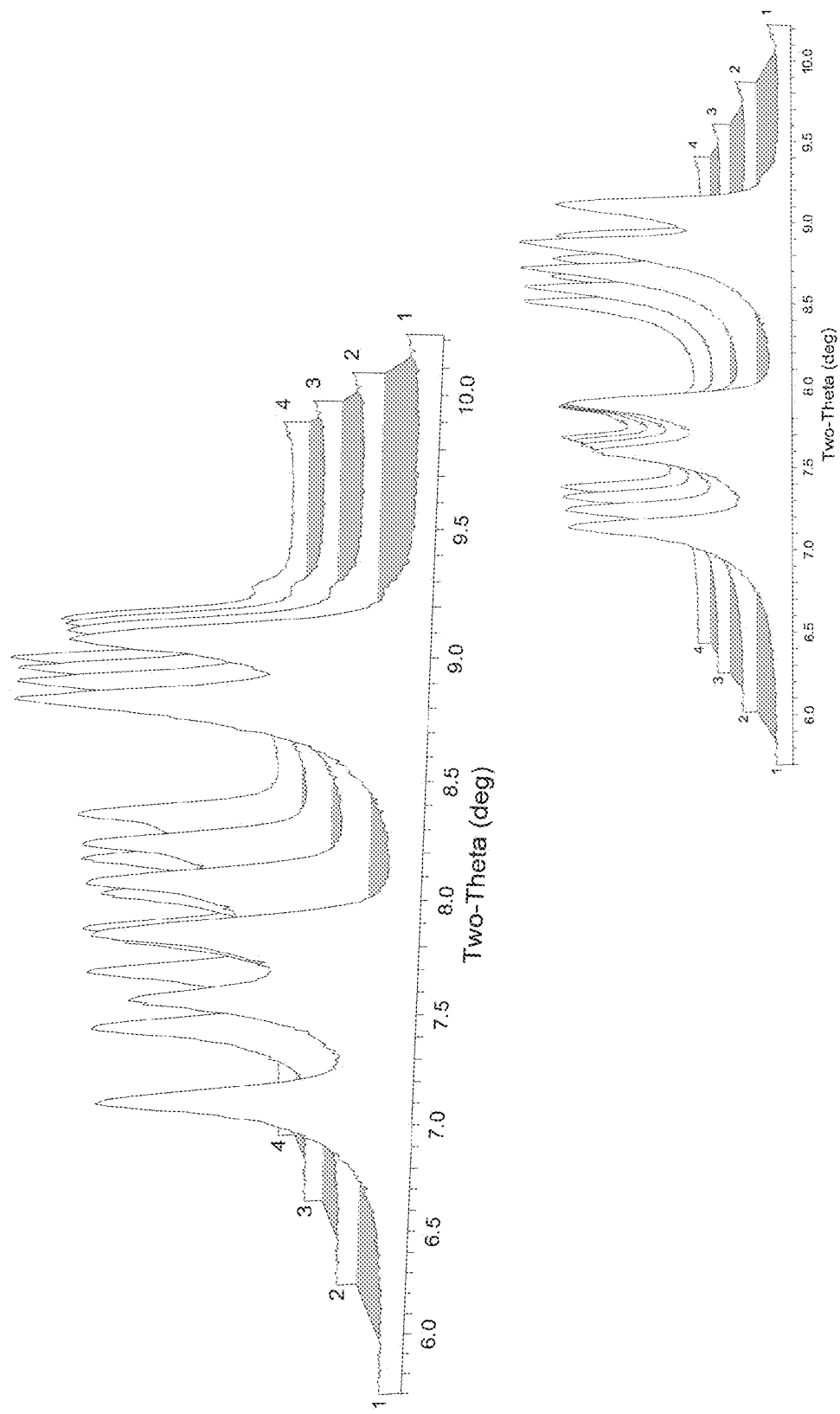
FIG. 12 is a plot of the low angle region in XRD analysis of materials showing that small percentages of IMF can be determined in samples largely consisting of TUN.

Rietveld analysis was able to quantify the level of IMF in the UZM-39 coherently grown composite structure at the 10% or greater level, however visually, small percentages of IMF can be determined in samples (FIG. 12) largely consisting of TUN at the 5% or greater level from intensity of peak at d-spacing of ~9.46 A, while at higher levels, other peaks can be followed such as the increase in peak at d-spacing of ~11.4 A amongst others. In FIG. 12, spectrum 1 is 1% IMF, 99% TUN; spectrum 2 is ~3% IMF, 97% TUN; spectrum 3 is ~5% IMF, 95% TUN; and spectrum 4 is ~10% IMF, 90% TUN.

Figure 13:
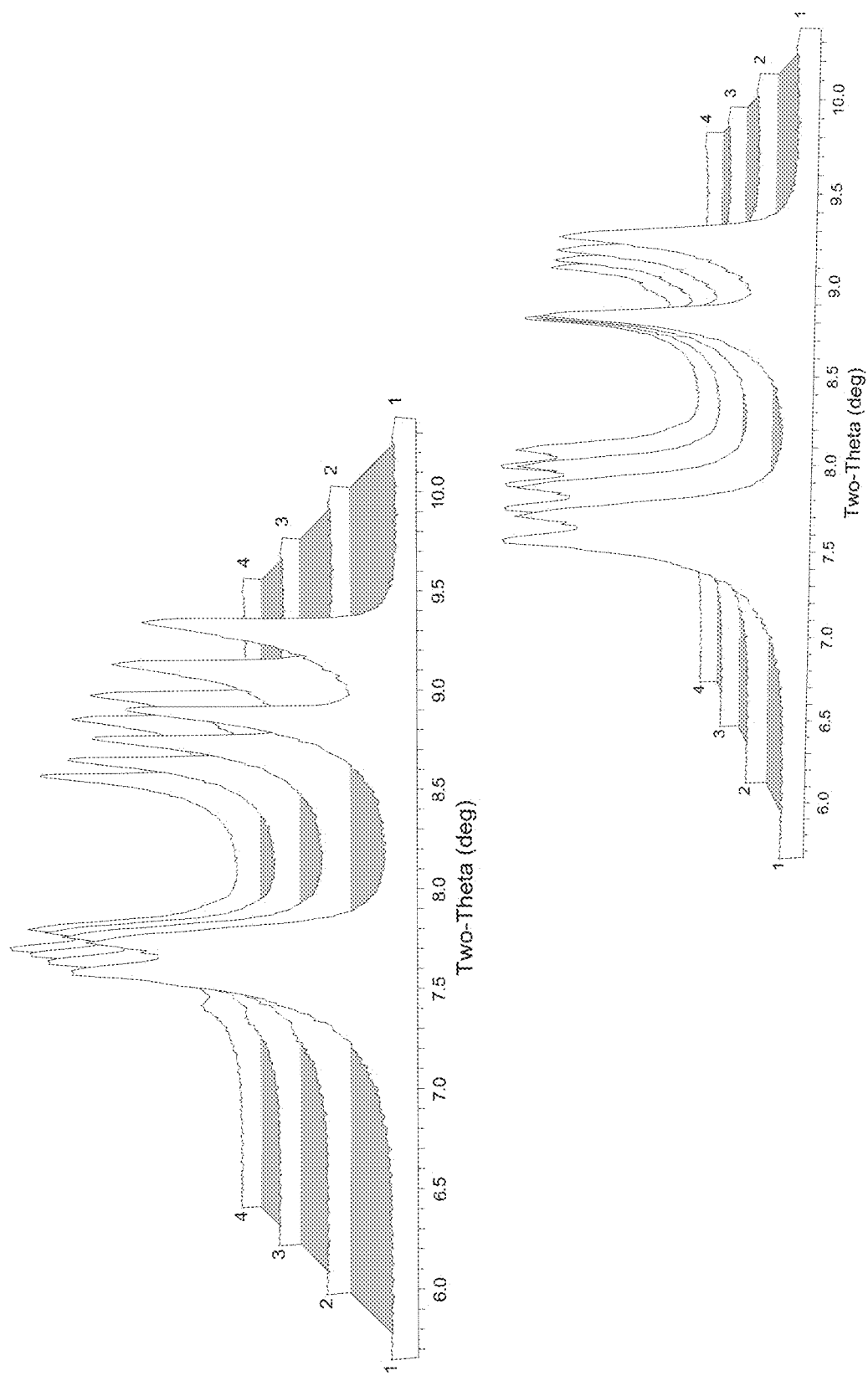
FIG. 13 is a plot of the low angle region in XRD analysis of materials showing that small percentages of TUN can be determined in samples largely consisting of IMF.

Rietveld analysis was able to quantify the level of TUN in the UZM-39 coherently grown composite structure at the 10% or greater level, however FIG. 13 shows that, visually, small percentages of TUN can be seen in samples largely consisting of IMF at the 5% or greater level from intensity of peak at d-spacing ~12.25 A, while at higher levels, other peaks can be followed such as the increase in peak at d-spacing of ~9.63 A amongst others. In FIG. 13, spectrum 1 is ~1%

TUN, 99% IMF; spectrum 2 is –3% TUN, 97% IMF; spectrum 3 is –5% TUN, 95% IMF; and spectrum 4 is –10% TUN, 90% IMF.

EXAMPLE 31

44.9 g of NaOH, (97%) was dissolved in 1122.3 g water. To this solution was added 10.8 g liquid sodium aluminate (22.9% $Al_2O_3$, 20.2% $Na_2O$) followed by 105.9 g Ultrasil VN3 (90% $SiO_2$, available from Evonik) to form a first mixture. Separately, 53.5 g 1,4-dibromobutane, (99%), was combined with 62.6 g 1-methylpyrrolidine, (97%) to form a second mixture. The second mixture was added to the first mixture to create the final reaction mixture. Last, 1 g of the layered material UZM-8 was added and the mixture was stirred vigorously for 1-2 hours before transferring to a 2 L stirred autoclave. The final reaction mixture was digested at 160° C. for 7 days while stirring at 200 rpm. The product was isolated by filtration and identified as UZM-39 by XRD. Analytical results showed this material to have the following molar ratios, Si/Al of 12.40, Na/Al of 0.21, N/Al of 1.10, C/N of 7.06.

EXAMPLE 32

NaOH, $Al(OH)_3$, $Ga(NO3)3·9H_2O$, Ludox AS-40, 1,4-dibromobutane, 1-methylpyrrolidine, water and layered material UZM-8 were combined to form a mixture of composition $0.5Al_2O_3:0.5Ga_2O_3:65.4SiO_2:24.6Na_2O:9.9\ C_4Br_2:29.4\ 1\text{-}MP:2636H_2O$ and stirred vigorously for 1-2 hours before transferring to a 2 L stirred autoclave. The final reaction mixture was digested at 160° C. for 150 hours while stirring at 250 rpm. The product was isolated by filtration and identified as UZM-39 by XRD. Analytical results showed this material to have the following molar ratios, Si/Al of 21.61, Si/Ga of 31.35, Si/(Al+Ga) of 12.79, Na/(Al+Ga) of 0.10, N/(Al+Ga) of 0.91, C/N of 7.39.

EXAMPLE 33

A UZM-39 containing a high quantity of TUN and low quantity of IMF in the H+ form was loaded into a vertical steamer. The UZM-39 was exposed to 100% steam at 725° C. for 12 hours or 24 hours. The starting UZM-39 had a BET surface area of 385 m²/g, pore volume of 0.248 cm³/g, and micropore volume of 0.180 cm³/g. After 12 hours of steaming, the UZM-39 was still identified as UZM-39 by XRD though the intensity of the first 5 peaks had increased to strong, strong, very strong, strong and medium respectively. All other peaks were at positions and intensities described in Table B. The material had a BET surface area of 331 m²/g, pore volume of 0.243 cm³/g, and micropore volume of 0.151 cm³/g. After 24 hours of steaming, the UZM-39 was still identified as UZM-39 by XRD though the intensity of the first 5 peaks had increased to medium-strong, strong, strong, medium-strong and medium respectively. All other peaks were at positions and intensities described in Table B. The material had a BET surface area of 327 m²/g, pore volume of 0.241 cm³/g, and micropore volume of 0.150 cm³/g.

EXAMPLE 34

A UZM-39 containing a high quantity of TUN and low quantity of IMF in the H+ form was put into a round bottom flask containing 6N $HNO_3$ and outfitted with a condenser and stirrer. The mixture containing UZM-39 and $HNO_3$ was boiled at reflux for 8 or 16 h. The resulting material was filtered, washed and dried. XRD analysis showed the material to be UZM-39 consistent with Table B.

EXAMPLE 35

The product generated by the synthesis described in Example 1 was bound with $SiO_2$ in a 75:25 weight ratio by combining 6.71 g Ludox AS-40, 8.31 g UZM-39 and 10.79 g water. This mixture was then evaporated while stirring to form the bound UZM-39/$SiO_2$. The bound material was then calcined using a 2° C./minute ramp to 550° C., holding for 3 hours and then cooling to room temperature. The 20 to 60 mesh fraction was isolated and then used as the catalytic composite in a chemical reaction to form ethylbenzene and xylenes.

Benzene and propane were fed at a 2:1 mole ratio into a reactor at 410 psig along with a hydrogen stream such that the hydrogen to hydrocarbon mole ratio was about 3.5. Multiple conditions where then set starting at about 425° C. and 1.8 LHSV (Table 2 Column 1) and continuing to 485° C. and 1.8 LSVH (Table 2 Column 2); continuing again to 535° C. and 1.8 LHSV (Table 2 Column 3); continuing again to 535° C. and 3 LHSV (Table 2 Column 4); and finally continuing to 575° C. and 3 LHSV (Table 2 Column 5). Table 2 shows the percent of benzene and propane conversion to other compounds.

TABLE 2

| Percent Conversion | Column 1 | Column 2 | Column 3 | Column 4 | Column 5 |
|---|---|---|---|---|---|
| Benzene | 7.43 | 16.15 | 26.19 | 22.90 | 26.79 |
| Propane | 57.58 | 61.58 | 81.35 | 68.79 | 86.50 |

The invention claimed is:

1. A separation process comprising contacting at least two components with a material to generate at least one separated component, wherein the material is a coherently grown composite of TUN and IMF zeotypes having a three-dimensional framework of at least $AlO_2$ and $SiO_2$ tetrahedral units and an empirical composition in the hydrogen form after calcination, ion-exchange and calcination and on an anhydrous basis expressed by an empirical formula of

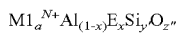

and where M1 is at least one exchangeable cation selected from the group consisting of alkali, alkaline earth metals, rare earth metals, zinc, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, "x" is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

and is characterized in that it has the x-ray diffraction pattern having at least the d-spacings and intensities set forth in Table B1:

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections.

2. The process of claim 1 wherein the separation is based on molecular size of the components, degree of polarity of the components, or ion exchange of the components with the material.

* * * * *